(12) United States Patent  (10) Patent No.: US 7,798,988 B2
Aubert et al.  (45) Date of Patent: Sep. 21, 2010

(54) IMPLANT BACK-INJECTING DEVICE

(75) Inventors: Christophe Aubert, Cudrefin (CH);
Roland Cherif-Cheikh, Barcelona (ES);
Thierry Rimlinger, L'Isle d'Abeau
(FR); Fabrice Bonacci, Saint Priest
(FR); Serge Barneaud, Puget Theniers
(FR); Grant Timothy Lewis Smetham,
Westcott Nr Dorking (GB); **Julian
Richard Dixon**, Cambridge (GB);
Matthew Egerton Young, Cambs (GB)

(73) Assignee: **Sociétéde Conseils de Recherches et
d'Applications Scientifiques
(S.C.R.A.S) SAS**, Paris (FR)

( * ) Notice: Subject to any disclaimer, the term of this patent is extended or adjusted under 35 U.S.C. 154(b) by 109 days.

(21) Appl. No.: 11/720,538

(22) PCT Filed: Dec. 1, 2005

(86) PCT No.: PCT/EP2005/012825

§ 371 (c)(1),
(2), (4) Date: Mar. 19, 2008

(87) PCT Pub. No.: WO2006/058745

PCT Pub. Date: Jun. 8, 2006

(65) Prior Publication Data

US 2008/0249466 A1 Oct. 9, 2008

(30) Foreign Application Priority Data

Dec. 1, 2004 (EP) .................................. 04028411
Dec. 1, 2004 (EP) .................................. 04028412
Dec. 1, 2004 (EP) .................................. 04028413

(51) Int. Cl.
*A61M 31/00* (2006.01)
(52) U.S. Cl. ....................... 604/57; 604/117
(58) Field of Classification Search ............ 604/57, 604/59, 60, 117
See application file for complete search history.

(56) References Cited

U.S. PATENT DOCUMENTS 5,284,479 A   2/1994   de Jong
5,300,079 A * 4/1994   Niezink et al. ............. 606/117

(Continued)

FOREIGN PATENT DOCUMENTS

EP   0 596 162 A1   5/1994

(Continued)

OTHER PUBLICATIONS

International Search Report issued in corresponding application No. PCT/EP2005/012825, completed Mar. 30, 2006 and mailed May 3, 2007.

*Primary Examiner*—Nicholas D Lucchesi
*Assistant Examiner*—Gerald Landry, II
(74) *Attorney, Agent, or Firm*—Griffin & Szipl, P.C.

(57) ABSTRACT

The invention concerns a device for back injecting an implant (30) into the skin (22) of a subject, said device (1) include a hollow main body (10), to which a hollow needle (28) is fixed into which the implant (30) is introduced, a secondary body (12; 114) coaxially arranged inside the main body (10) and surrounding the needle (28) and a piston rod (88) able to slide coaxially inside said hollow needle (28) and whose position relative to said needle (28) remains unchanged when the back injection device (1) is pressed against the subject's skin (22) to allow the needle (28) to penetrate said subject's skin and when the secondary body (12) retracts inside the main body (10), the piston rod (88) penetrating the interior of the hollow needle (28) to hold the implant (30) at the required depth in the subject's skin (22) during withdrawal of the hollow needle (28) from the subject's skin (22), during which the secondary body (12; 114) exits the main body (10), characterized in that it includes means for the elastic return of the secondary body (12) from the main body (10).

33 Claims, 40 Drawing Sheets

U.S. PATENT DOCUMENTS

| | | |
|---|---|---|
| 5,562,613 A | 10/1996 | Kaldany |
| 6,228,049 B1 | 5/2001 | Schroeder et al. |
| 6,402,716 B1 * | 6/2002 | Ryoo et al. .................. 604/60 |
| 2002/0161337 A1 * | 10/2002 | Shaw et al. ................. 604/197 |
| 2003/0004457 A1 | 1/2003 | Andersson |
| 2003/0040699 A1 * | 2/2003 | Talling et al. ................ 604/60 |
| 2003/0233101 A1 | 12/2003 | Lubock et al. |
| 2005/0101967 A1 * | 5/2005 | Weber et al. ................ 606/107 |

FOREIGN PATENT DOCUMENTS

| | | |
|---|---|---|
| EP | 0 783 342 B1 | 11/1998 |
| EP | 1 666 085 A1 | 7/2006 |

\* cited by examiner

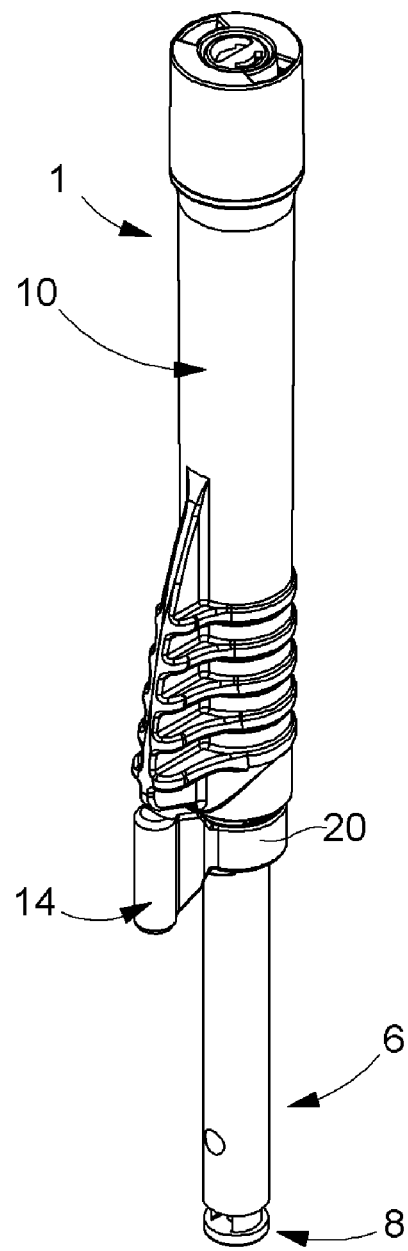
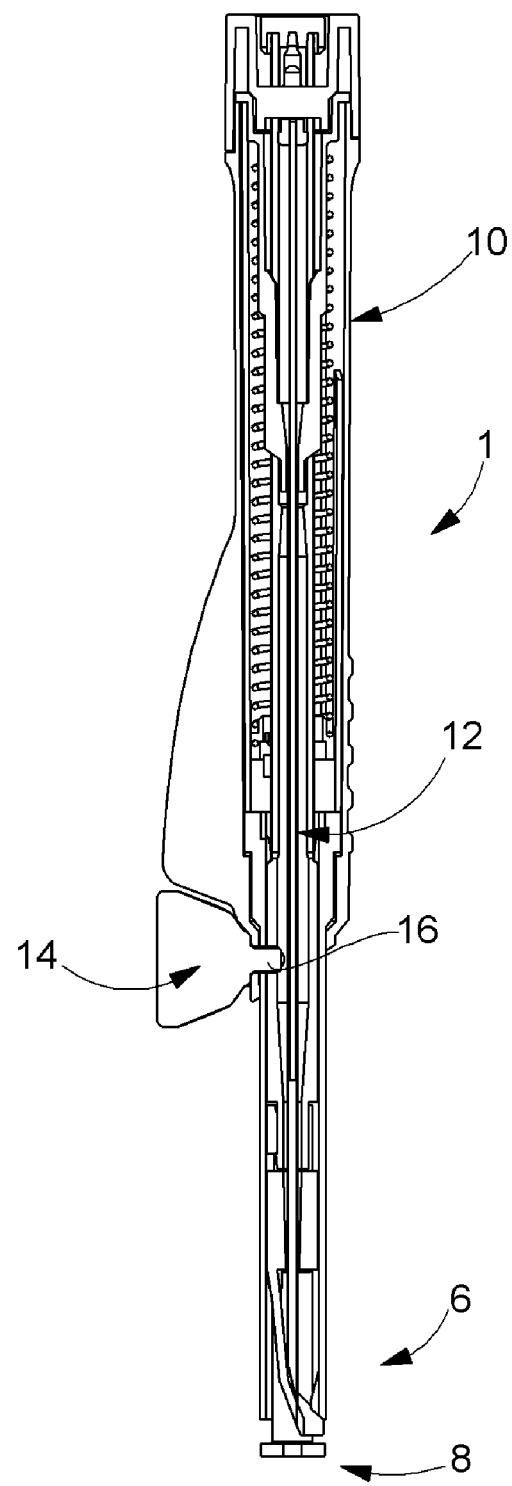
Fig. 2A
Fig. 2B

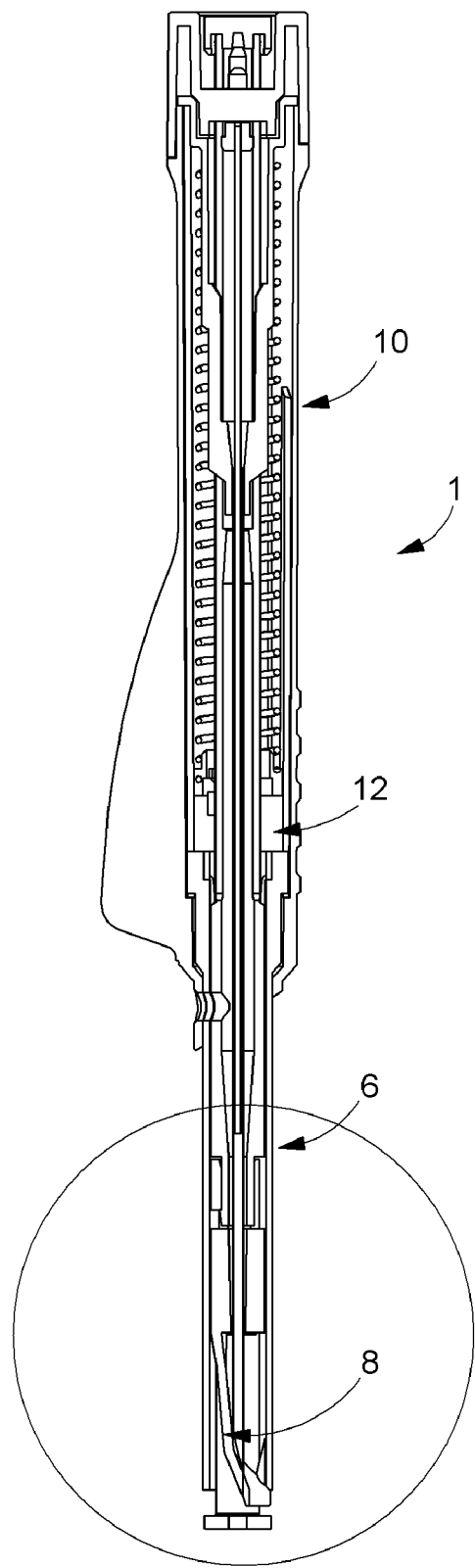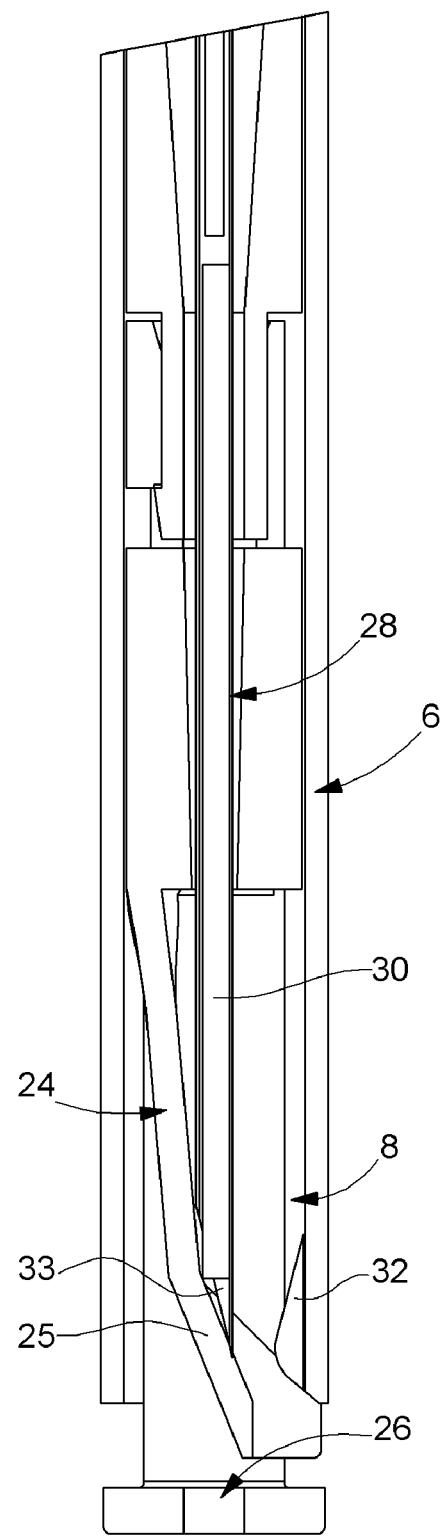
Fig. 4A
Fig. 4B

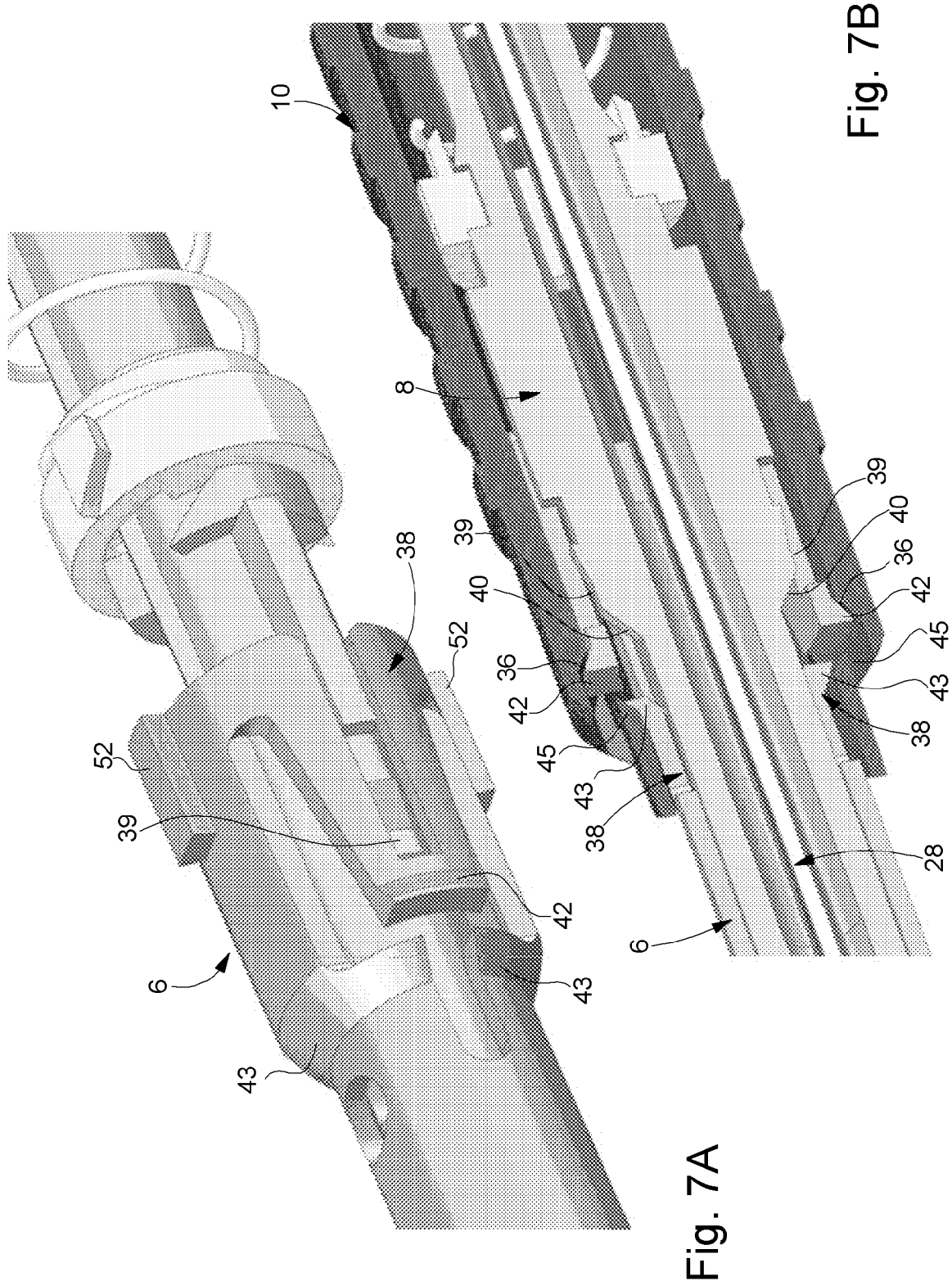

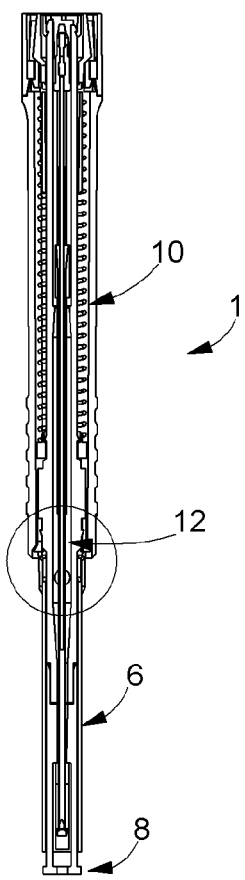
Fig. 8A
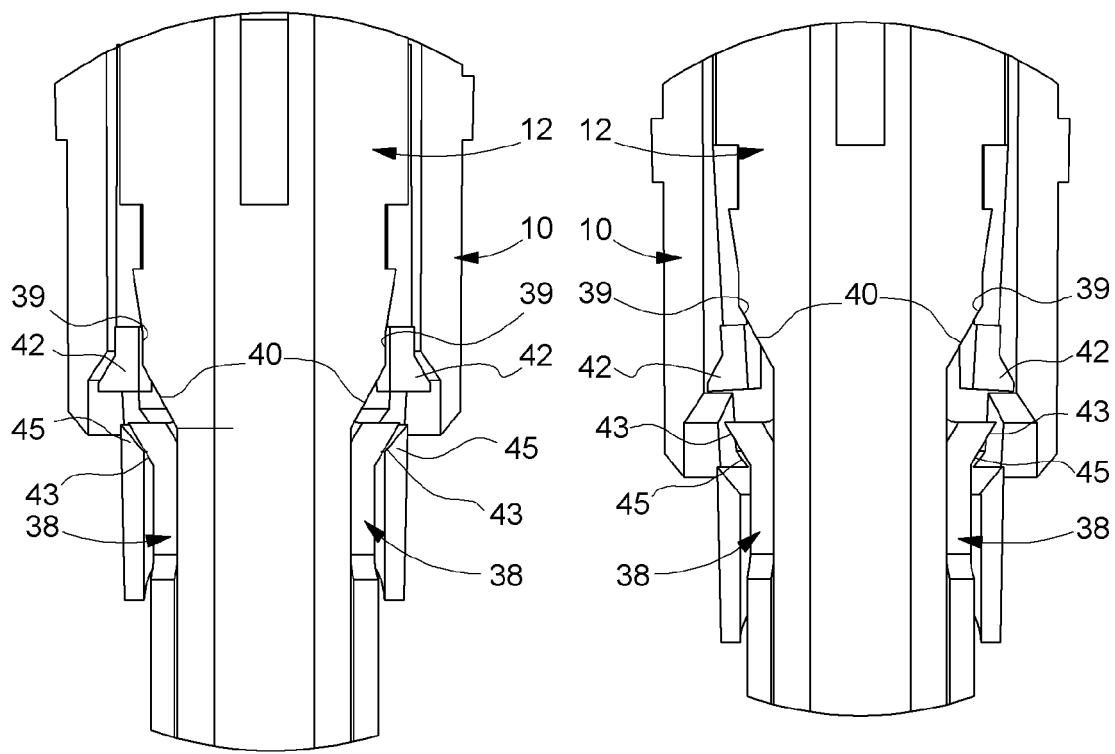
Fig. 8B                    Fig. 8C

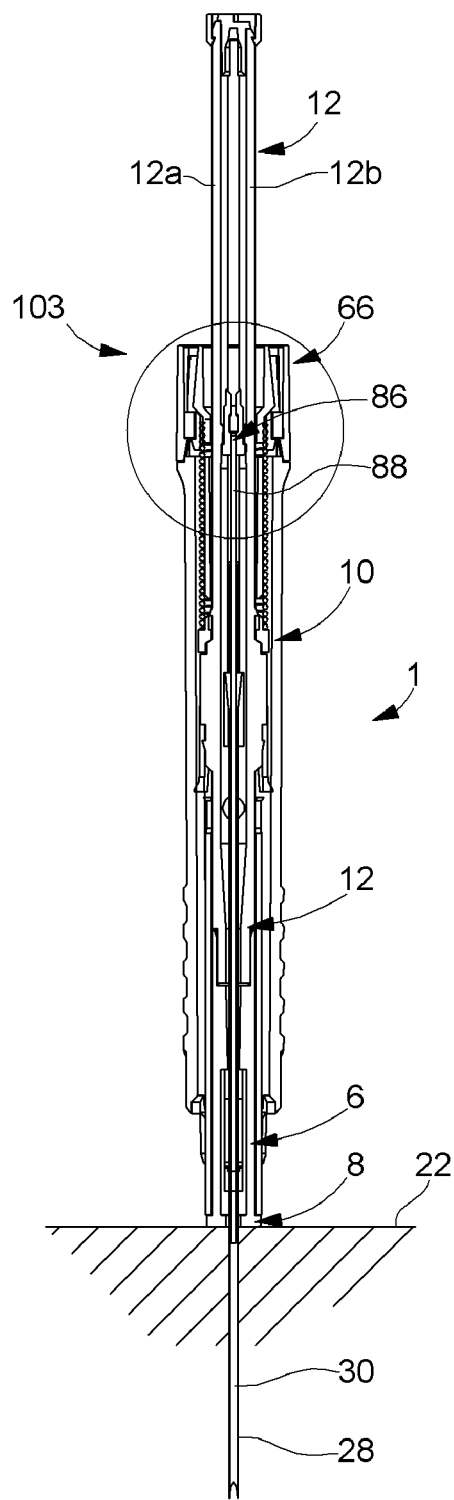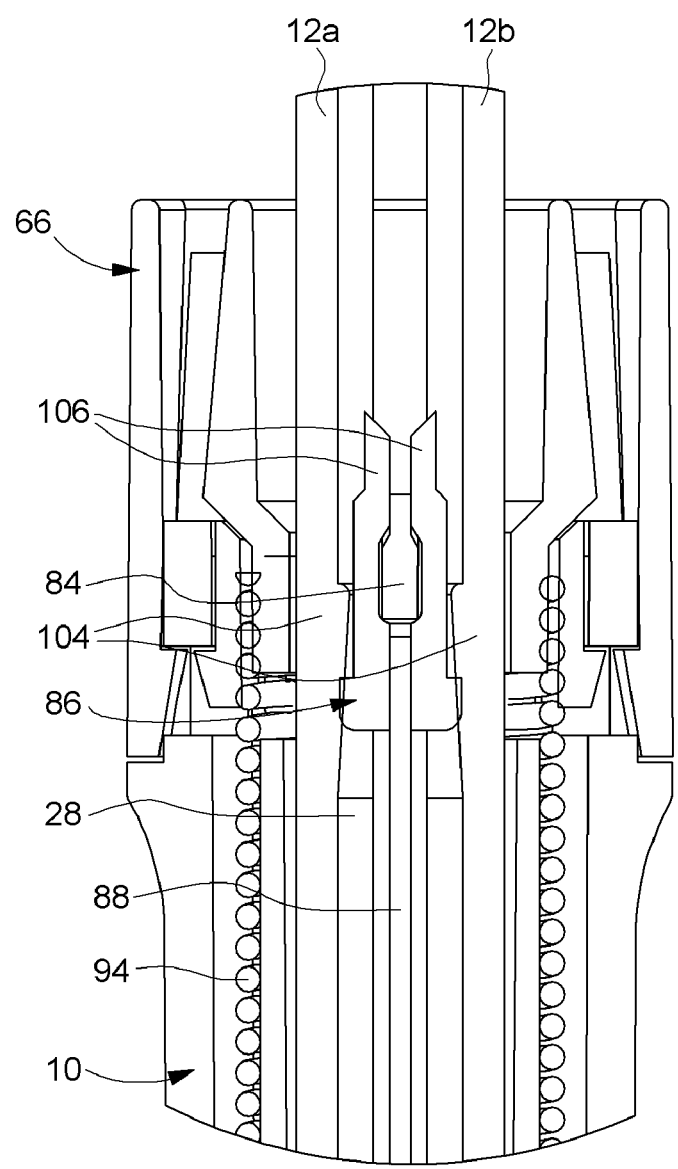
Fig. 17A
Fig. 17B

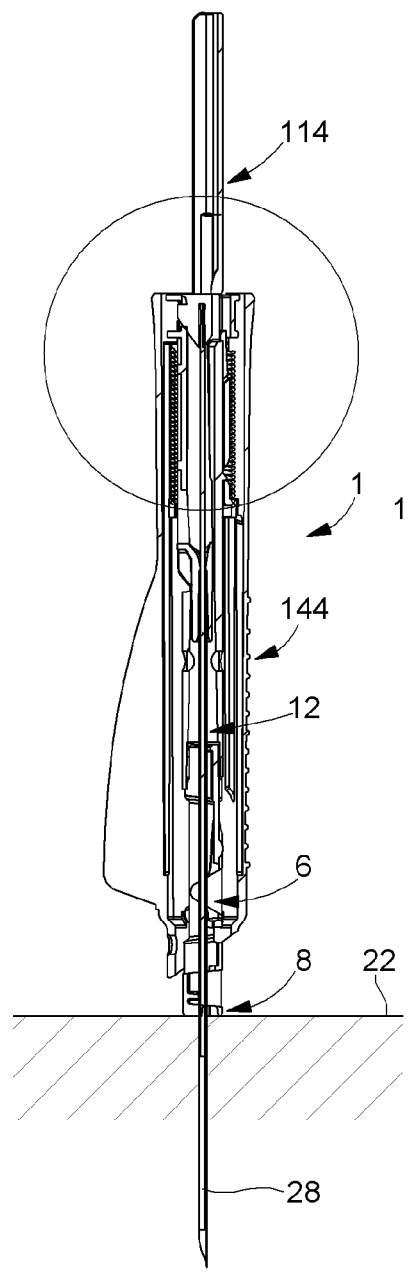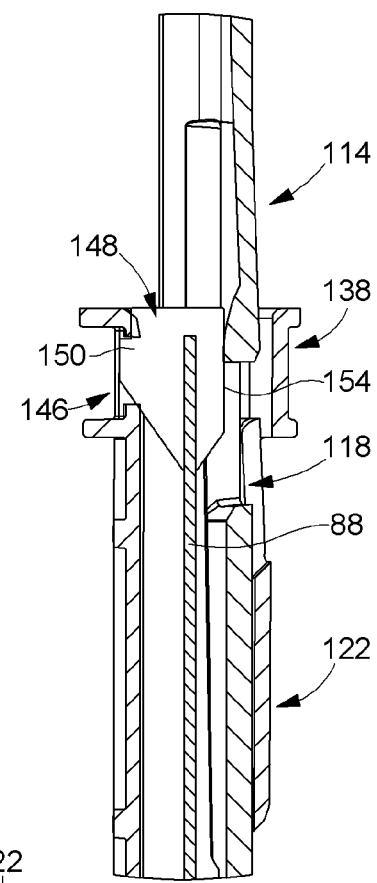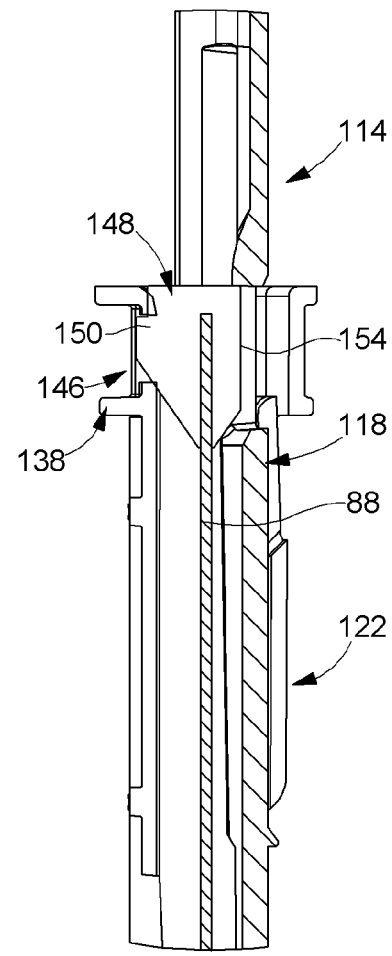
Fig. 27A
Fig. 27B
Fig. 27C

IMPLANT BACK-INJECTING DEVICE

This is a National Phase Application in the United States of International Patent Application No. PCT/EP2005/012825 filed Dec. 1, 2005, which claims priority on European Patent Applications No. 04028413.5, 04028411.9 and 04028412.7, all filed Dec. 1, 2004. The entire disclosures of the above patent applications are hereby incorporated by reference.

FIELD OF THE INVENTION

The present invention concerns an injection device and, in particular, a device for the intramuscular or subcutaneous injection of an active pharmaceutical principle in the solid or semisolid state, usually called an implant. More generally, the invention applies to the injection of a solid body for human or animal use such as for example electronic chips used for identifying a living being.

BACKGROUND OF THE INVENTION

Implant back injection devices of the type with which the present invention is concerned conventionally comprise a main hollow body, secured to a hollow needle into which the implant to be injected is introduced. A secondary body, arranged coaxially inside the main body, surrounds the needle in which a piston rod is able to slide coaxially. The purpose of this piston rod is to ensure that the implant is deposited at the proper depth in the subject tissue. When this back injection device is pressed against the subject tissue, the main body starts to slide along the secondary body from a proximal position to a distal position to allow the needle to penetrate the subject tissue. The movement of the main body is accompanied by a simultaneous movement of the piston rod, which, when the needle is withdrawn from the subject tissue, remains fixed relative to the needle so as to allow the implant to be kept at the required depth in the subject tissue.

The method of use of such a back injection device is as follows. By holding the back injection device in one hand via its main body, the practitioner presses the distal end of the secondary body against the subject's skin. When the back injection device is suitably arranged, the practitioner pushes on the main body. Via the effect of this pressure, the main body starts to slide axially along the secondary body, allowing the needle, which is secured to said main body, to penetrate the subject's skin. At the same time, the main body drives the piston rod whose position relative to the needle and the implant therefore remains unchanged. It is at the moment that the needle has reached maximum penetration of the subject's tissue that the actual implant back injection operation occurs. Indeed, the practitioner, in a gesture not dissimilar to a conventional injection, will with his left hand if he is right handed, hold the back injection device against the subject's skin in order to minimise the movement of the needle and move his other hand so as to hold the secondary body against the skin via his thumb which presses on a button provided at the proximal end of the secondary body whereas, with his index finger and middle finger, he will control the return of the main body to its proximal position by using a finger rest fitted to said main body. During this gesture, the needle gradually exits the subject's tissue. The piston rod does not however accompany this movement of withdrawal by the main body. Indeed, retained by the secondary body, it is uncoupled from said main body and remains immobile, thus gradually penetrating the hollow needle as the latter exits the skin. The implant thus emerges from the needle, held in position at the correct depth in the skin via the distal end of the piston rod, which abuts against said implant. The piston rod is then uncoupled from the secondary body and coupled to the main body again such that the needle and the piston rod end the back injecting movement together in a position in which they are protected by the secondary body.

In course of use, it has been observed that the use of a back injection device of the type described above is not always convenient and is often misunderstood by practitioners. Indeed, a large number of practitioners think that the gesture is finished once the needle has penetrated as deep as possible into the subject tissue, omitting to carry out the back injecting operation which alone allows the implant to be deposited in the subject tissue. Other practitioners have attempted to carry out the back injecting gesture by placing their thumb on the button of the secondary body and passing their index and middle fingers under the finger rest as indicated. However, these practitioners hold the main body firmly in their other hand, which makes it impossible for the main body to return to its proximal position and thus for the needle to exit the subject tissue. More generally, it has been deemed inconvenient and painful for the subject to have to hold the back injection device in one hand to press it against the subject's skin and push in the needle, then to have to release said device in order to perform the back injecting gesture with the other hand.

It is an object of the present invention to overcome the aforementioned drawbacks in addition to others by providing an implant back injection device that simplifies as much as possible the implant injecting gesture under a subject's skin.

SUMMARY OF THE INVENTION

The present invention therefore concerns a device for back injecting an implant into a subject's skin, this device including a hollow main body fixed to a hollow needle, into which the implant is introduced, a secondary body arranged coaxially inside the main body and surrounding the needle, and a piston rod able to slide coaxially inside said hollow needle, whose position relative to said needle remains unchanged when the back injection device is pressed against the subject's skin to allow the needle to penetrate the skin of said subject and when the secondary body retracts inside the main body, the piston rod being driven inside the hollow needle to maintain the implant at the required depth in the subject's skin during withdrawal of the hollow needle from the subject's skin, characterized in that it includes elastic means for returning the secondary body from the main body.

Owing to these features, the present invention provides a device for back injecting an implant that needs only to be pressed against the subject's skin until the needle has completely penetrated the skin, the secondary body then automatically exiting the main body to cover the needle gradually as the back injection device is moved away from the subject's skin and the implant injection operation is carried out. The implant injection operation is thus entirely automated as soon as the needle is inserted into the tissue, which makes it as simple as possible and in particular removes the relatively complicated back injecting gesture which had to be performed with the devices of the prior art. Moreover, it is not necessary to change the manner in which the device according to the invention is held during the implant back injecting operation, which also facilitates the practitioner's work. It should also be noted that the secondary body caps the hollow needle, into which the implant is introduced, before and after the injection, which prevents any risk of scratch or contamination of the needle and the practitioner.

According to a complementary feature of the invention, the back injection device includes a retaining element for preventing the implant from falling prior to the use of said device.

According to a first variant, the retaining element includes an elastic tongue which, in the rest position, via an end part bent towards the inside of the volume of the retaining element, closes the hole for the passage of the hollow needle and which, when the back injection device is pressed against the subject's skin, moves away to free the passage for said hollow needle.

According to a second variant, the retaining element includes an elastic tongue above which the hollow needle passes and which, in the storage position of the back injection device, is bent towards the inside of the volume of said retaining element, such that the needle is moved away from its general forward direction, the elastic tongue covering its rest position in which it enables said needle to be realigned and to move forward when said back injection device is pressed against the subject's skin.

These two variants of the implant retaining device have a common advantage, which lies in the fact that the hollow needle does not have to push via its bevel against an element of the injection device in order to pave its way towards the exit of said device. The needle bevel is not therefore likely to be damaged and the risks of injecting into the subject's skin fragments of the plastic material of which the injection device is made are avoided.

According to another feature of the invention, the back injection device further includes a sheath, which cooperates with the secondary body to allow the back injection device to be irreversibly locked after use. More specifically, the secondary body is locked onto the sheath, which is itself locked onto the main body.

The back injection device is thus totally locked after use, which makes any subsequent re-use of the device impossible and especially prevents any risk of the practitioner pricking himself with the soiled needle.

According to yet another feature of the invention, the sheath also temporarily locks the back injection device before use.

The back injection device is only activated at the moment when it is pressed against the subject's skin, which removes any possibility of the practitioner accessing the needle prior to carrying out the injection and soiling the needle by pricking himself.

According to yet another feature of the invention, the elastic return means include a spring which, at one of its ends, abuts on the secondary body, and which, at its other end, abuts against a base that carries the hollow needle and which is secured to the main body.

When the needle is pushed into the subject's skin, the collar moves upward by sliding axially inside the main body, such that the spring compresses. Then, when it reaches a turning point which corresponds to the maximum point of penetration of the needle into the skin, the collar pivots and slides again in the opposite direction in the main body, which allows the spring to be let down. Thus, with the exception of the collar, all of the moving parts of the back injection device according to the invention move only axially, which guarantees reliable operation of the device. Indeed, when the back injection device is pressed against the subject's skin, this generates friction forces that could interfere with the proper operation of the device if the part in contact with the skin had to perform a pivoting movement.

According to a first variant, the secondary body is a hollow body of substantially cylindrical shape provided with two rectilinear, diametrically opposite slots which extend from the proximal end of said secondary body to a determined height above the distal end of the back injection device, these slots defining two tube portions.

According to a second variant, the secondary body includes a single tube portion.

This second variant is preferred to the first in that it avoids tolerance problems linked to the manufacture of various parts forming the back injection device.

BRIEF DESCRIPTION OF THE DRAWINGS

Other features and advantages of the present invention will appear more clearly from the following detailed description of an embodiment of the back injection device according to the invention, this example being given purely by way of non-limiting illustration, in conjunction with the annexed drawing, in which:

FIG. 2A is a longitudinal cross-section of the back injection device after the cap has been removed;

FIG. 2B is a longitudinal cross-section of the back injection device shown in FIG. 2A;

FIG. 4A is a longitudinal cross-section of the back injection device fitted with means for retaining the implant according to a first variant;

FIG. 4B is a larger scale view of the zone surrounded by a circle in FIG. 4A;

FIG. 7A is a partial perspective view of the sheath, secondary body and collar;

FIG. 7B is a longitudinal cross-section of the parts shown in FIG. 7A;

FIG. 8A is a longitudinal cross-section of the back injection device according to the invention in the rest position;

FIG. 8B is a larger scale view of the zone surrounded by a circle in FIG. 8A, the sheath being locked onto the main body via the secondary body;

FIG. 8C is a similar view to that of FIG. 8A, the secondary body having slightly penetrated the interior of the main body, thereby uncoupling the sheath from said main body;

FIG. 17A is a larger scale detail view of the back injection device at the moment when the needle has penetrated to a maximum the subject's skin;

FIG. 17B is a larger scale detail view of the zone surrounded by a circle in FIG. 17A, the piston rod head being coupled to the main body;

FIG. 27A is a longitudinal cross-section of the back injection device including a secondary body according to the second embodiment at the moment when the needle has reached maximum penetration into the subject's tissue;

FIG. 27B is a larger scale detail view of the zone surrounded by a circle in FIG. 27A just before the piston rod head is coupled to the secondary body;

FIG. 27C is a similar view of FIG. 27B showing the piston rod head coupled to both the main body and the secondary body;

DETAILED DESCRIPTION OF THE ILLUSTRATIVE EMBODIMENTS

Hereafter, the "proximal" end means the end located on the side of the practitioner, and the "distal" end means the end located on the side of the subject to whom the injection is being administered.

Figure 1A:
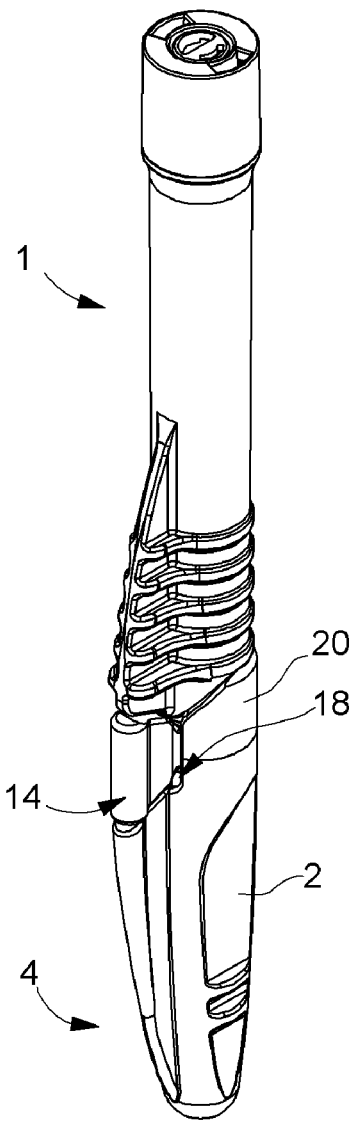
FIG. 1A is a perspective view of the back injection device according to the invention in the storage position.
Figure 1B:
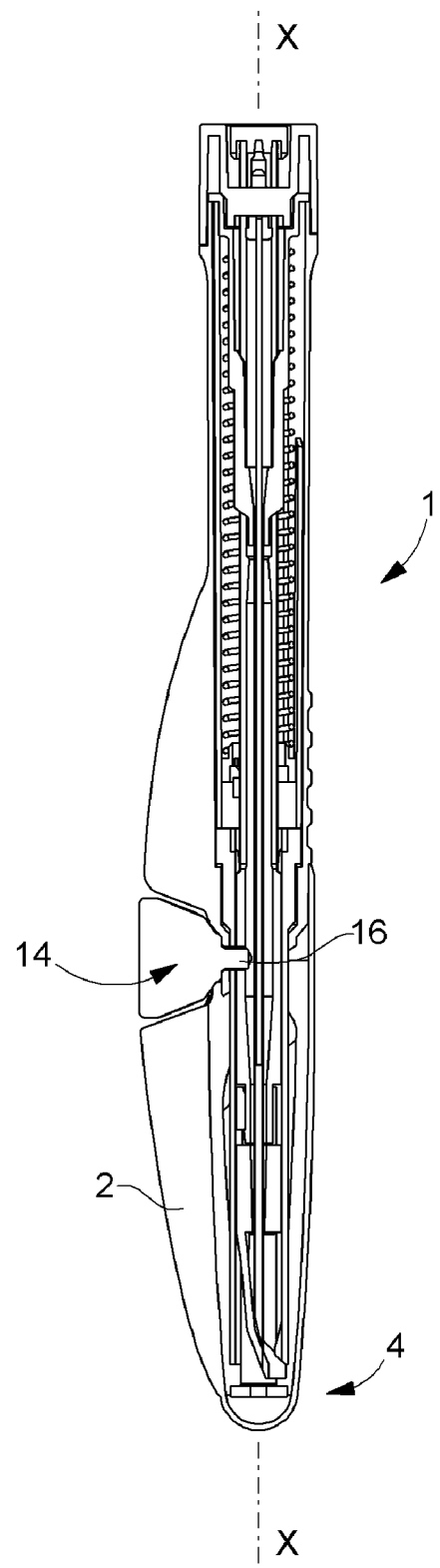
FIG. 1B is a longitudinal cross-section of the back injection device shown in FIG. 1A.
Figure 2C:
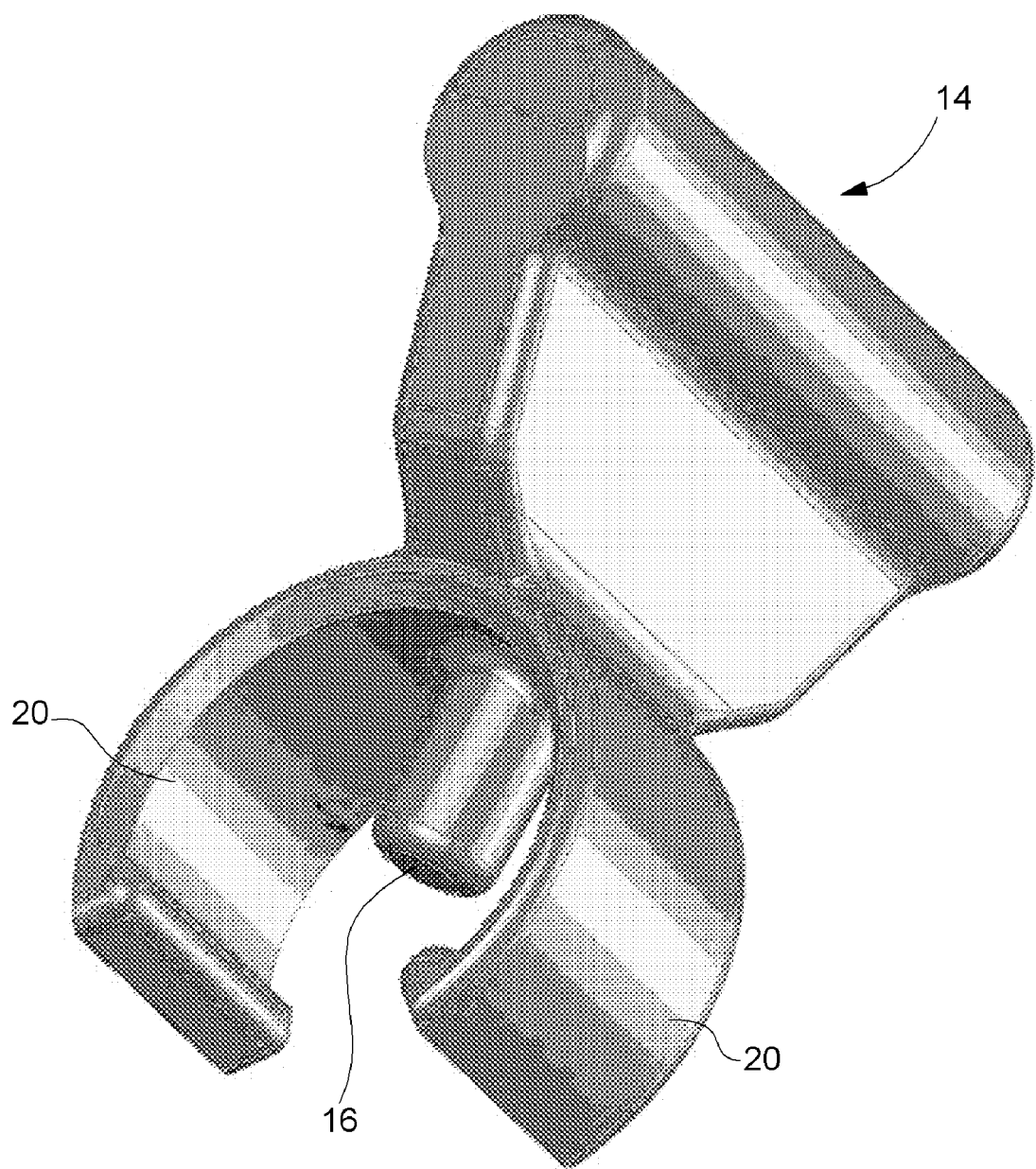
FIG. 2C is a perspective view of the staple shaped member.

One starts by removing the back injection device according to the invention from its secondary packaging (not shown). Designated as a whole by the general reference numeral 1, the back injection device includes first (see FIGS. 1A and 1B) a cap 2 that covers its distal end 4. In order to carry out the back-injection, this cap 2 must first of all be removed by exerting thereon a slight traction force along the longitudinal axis X-X of said back injection device 1. During this movement, a sheath 6 extended at the distal end thereof by a retaining element 8 is uncovered (see FIGS. 2A and 2B), these two elements projecting from the main body 10 of back injection device 1. As will be seen in more detail hereafter, retaining element 8 is secured to secondary body 2 that extends coaxially inside main body 10.

The back injecting operation cannot start until a staple shaped member 14 has also been removed, said staple shaped member (see FIG. 2C) having at the base thereof a stud 16 via which it is engaged in corresponding holes made respectively in main body 10, sheath 6 and secondary body 12. Thus, for as long as staple shaped member 14 is in place, main body 10, sheath 6 and secondary body 12 are coupled to each other, which makes any axial movement of these elements relative to the others impossible and therefore prevents the back-injection being carried out. It should be noted that cap 2 has a recess 18 via which it covers arms 20 of staple shaped member 14 which match the substantially circular shape of the distal end of main body 10. It is thus impossible to withdraw staple shaped member 14 before having removed cap 2, which offers additional security against any inadvertent activation of back injection device 1 according to the invention.

Figure 3:
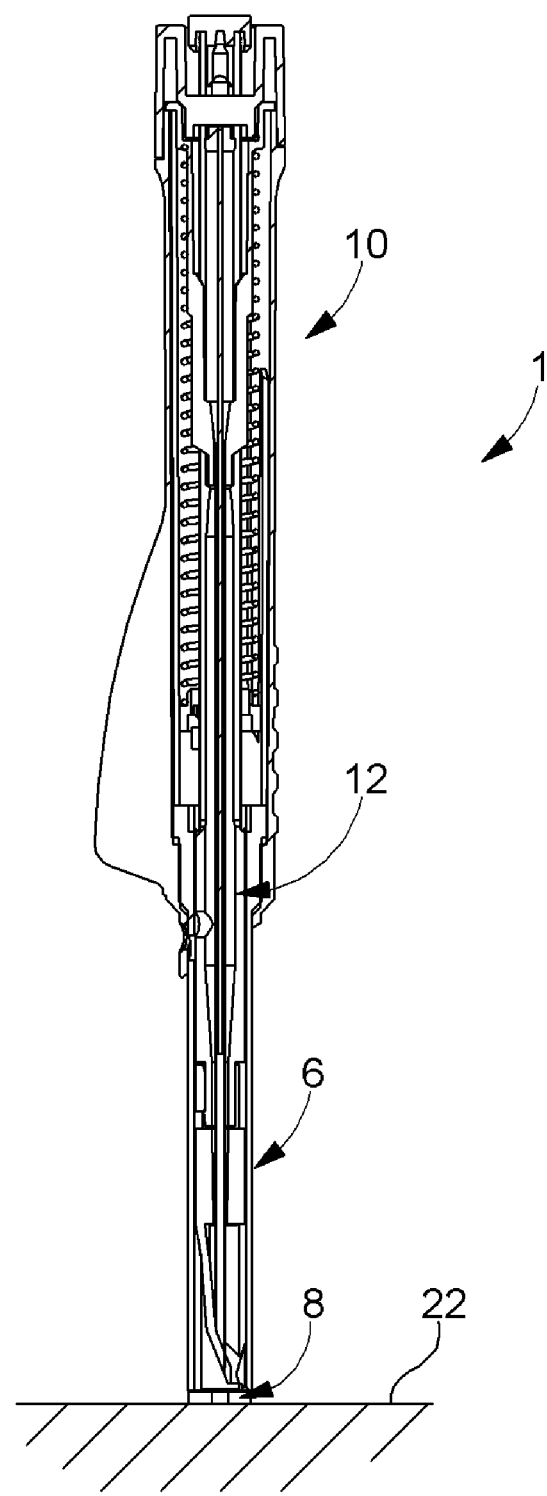
FIG. 3 is a longitudinal cross-section of the back injection device pressed against the subject's skin.
Figure 5A:
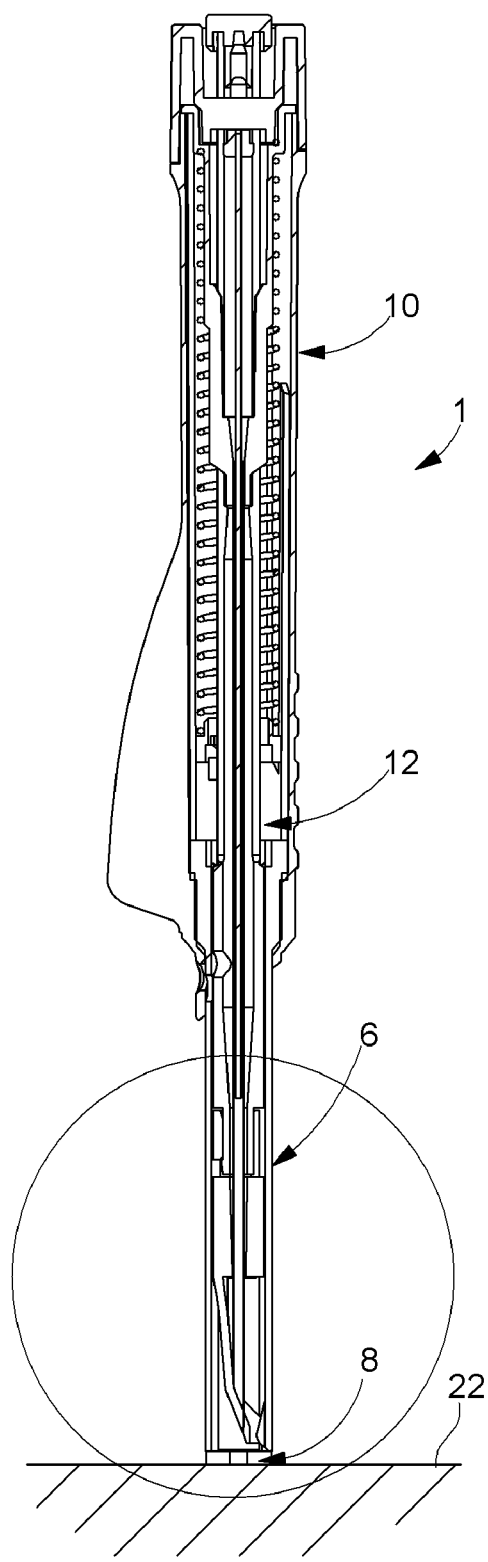
FIG. 5A is a similar view to that of FIG. 4A, the back injection device having been pressed against the subject's skin, the retaining means being moved apart to allow the needle to pass.
Figure 5B:
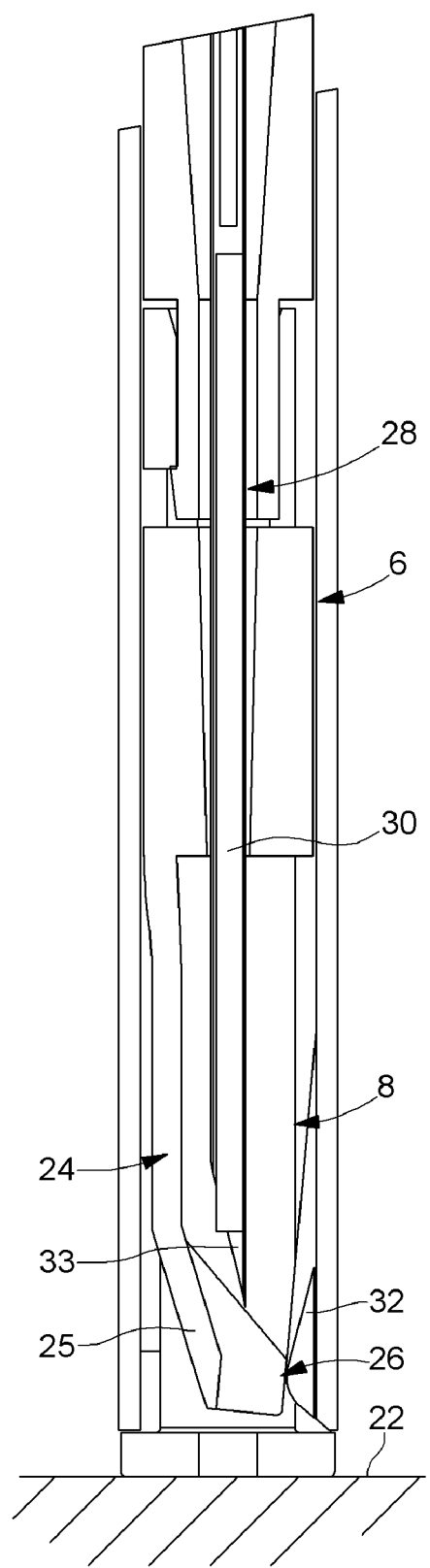
FIG. 5B is a larger scale view of the zone surrounded by a circle in FIG. 5A.
Figure 6A:
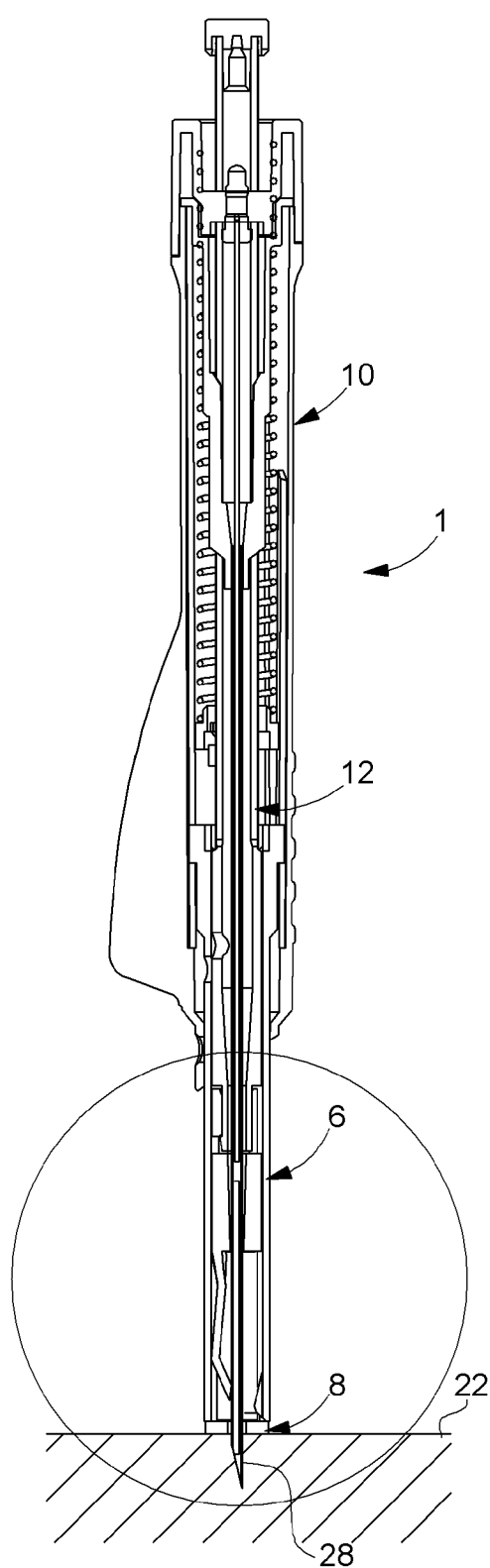
FIG. 6A is a similar view to that of FIG. 5A, the needle being pushed into the subject's skin.
Figure 6B:
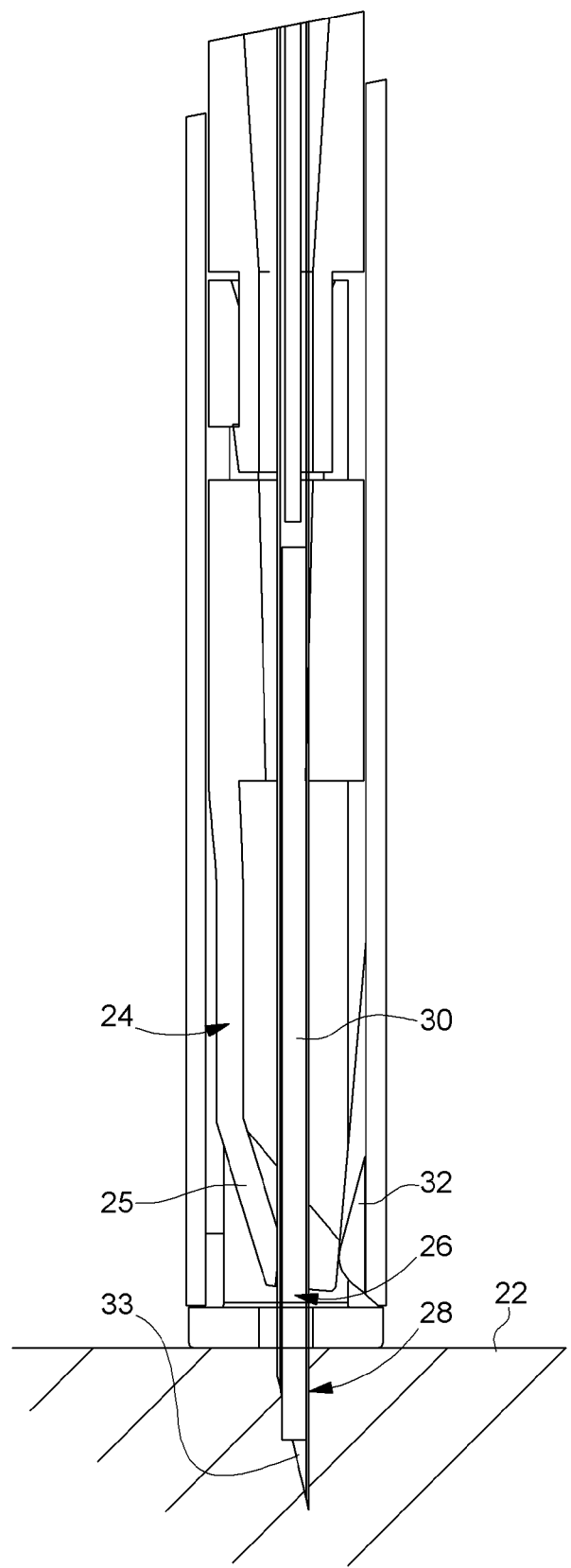
FIG. 6B is a larger scale view of the zone surrounded by a circle in FIG. 6A.

After removing cap 2 and staple shaped member 14, the actual back-injection operation may begin. In order to do this, the practitioner activates injection device 1 by pressing via its retaining element 8 against the subject's skin 22. Via the effect of this pressing, retaining element 8 slightly penetrates inside sheath 6 (see FIG. 3). This retaining element 8 includes (see FIGS. 4A and 4B) an elastic tongue 24, which, in the rest position, closes via an end part 25 bent towards the interior of the volume of retaining element 8, the clearance hole 26 for a hollow needle 28 arranged coaxially to the inside of secondary body 12 and in which the implant 30 to be administered to the subject is engaged. As sheath 6 has on the inner periphery of the distal end thereof two inclined planes 32 which will abut on elastic tongue 24 during the forward movement of retaining element 8 inside said sheath 6 (see FIGS. 5A and 5B), said tongue 24 will move away from its rest position and thus free the passage for needle 28 (see FIGS. 6A and 6B). Hollow needle 28 is thus not forced to pave a path by pushing, via its bevel 33, an element of device 1, which means that said bevel 33 is not damaged and there is no risk of injecting fragments of plastic material into the subject's skin 22. It will also be noted that the inclined planes 32 are used to index the position of retaining element 8 inside sheath 6. Thus, retaining element 8 has a rib that projects slightly relative to its outer cylindrical surface and which slides between said two inclined planes 32.

The main body 10 has on the inner periphery of the distal end thereof at least one, and preferably two diametrically opposite housings 36 into which two elastic substantially V-shaped arms 38 project provided at the proximal end of sheath 6 (see FIGS. 7A and 7B). These two arms 38 have two functions. The first of these functions is to temporarily immobilise said sheath 6 relative to said main body 10 in the storage position of the back injection device 1 according to the invention. The secondary body 12 thus has on the outer periphery thereof two diametrically opposite plane portions 39 which, in the storage position, hold elastic arms 38 of sheath 6 in housings 36 arranged in the inner surface of main body 10 (see FIG. 8B). It will be noted that the elastic arms 38 each have at their base a snug 42, which projects into the corresponding housing 36. Consequently, when back injection device 1 is pressed, via the distal end of its retaining element 8, against the subject's skin 22, said retaining element 8, secured to secondary body 12, slightly raises the latter inside main body 10, such that inclined planes 40 arranged on the outer periphery of said secondary body 12 move away from elastic arms 38 which are thus free to bend (see FIG. 8C). The snugs 42 are then released from their positioned engaged in housings 36, such that sheath 6 is uncoupled from main body 10 and is allowed to move up inside the latter. It will also be noted that sheath 6 has two truncated edges 43 via which it abuts against an inner shoulder 45 provided at the distal end of main body 10.

The second function of elastic arms 38 is the final locking of secondary body 12 on sheath 6 as will be described hereafter.

Figure 9A:
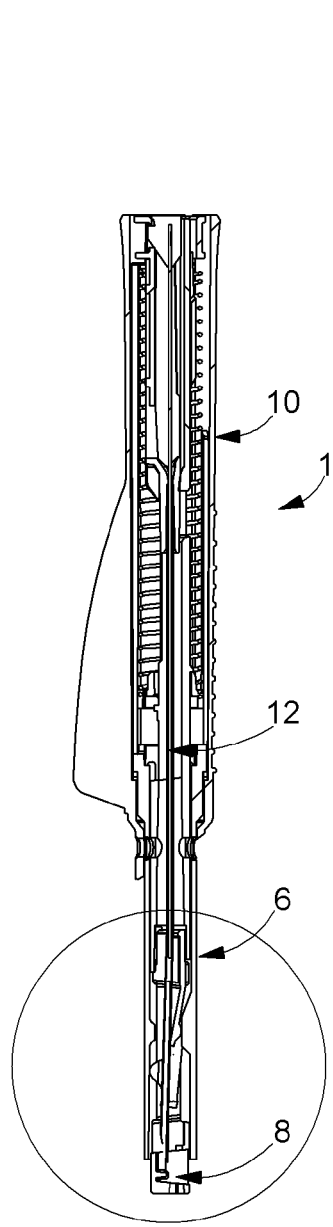
FIG. 9A is a longitudinal cross-section of the back injection device fitted with means for retaining the implant in accordance with a second variant.
Figure 9B:
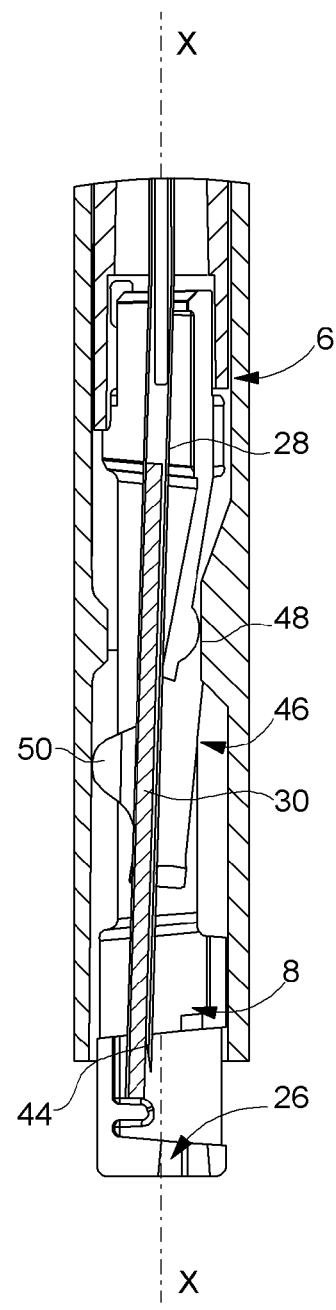
FIG. 9B is a larger scale view of the zone surrounded by a circle in FIG. 9A, the retaining means being in the rest position, preventing the implant from falling.
Figure 9C:
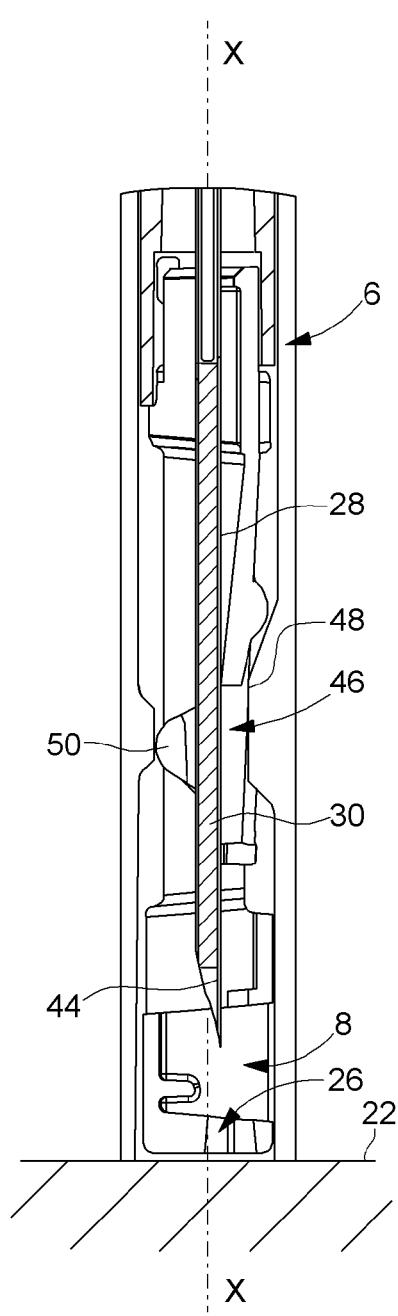
FIG. 9C is a similar view to that of FIG. 9B, the back injection device having been pressed against the subject's skin and the retaining means allowing the needle to align with its general axis of forward movement.

As was seen above, a first solution that can be envisaged for retaining hollow needle 28 and preventing implant 30 from falling prior to injection is to provide, on the path of said needle 28, an elastic tongue 24, which in the rest position, blocks bevel 33 of needle 28 and which in the activated position, is moved away from the path of needle 28 to enable the latter to move forward and implant 30 to be deposited in the subject's tissue. According to a preferred variant (see FIGS. 9A and 9B), retaining element 8 includes an elastic tongue 46 above which needle 28 passes and which, in the storage position of back injection device 1, is bent towards the inside of the volume of retaining element 8 by a snug 48 provided on the inner surface of sheath 6. Needle 28 is thus slightly moved away from its general direction of forward movement along the longitudinal axis of symmetry X-X of back injection device 1 such that, if the implant slides partially out of needle 28 via the effect of its weight, it will abut against the distal end of retaining element 8, which will prevent it from falling. Subsequently, when back-injection device 1 is pressed against the subject's skin 22, retaining element 8 slightly penetrates the interior of sheath 6, such that snug 48 moves away from tongue 46 which returns to its rest position and which allows needle 28 to align itself along the longitudinal axis of symmetry X-X of injection device 1 and clearance hole 26. Additionally, an arch 50 may be provided at the end of tongue 46 for better axial guiding of hollow needle 28.

Figure 12A:
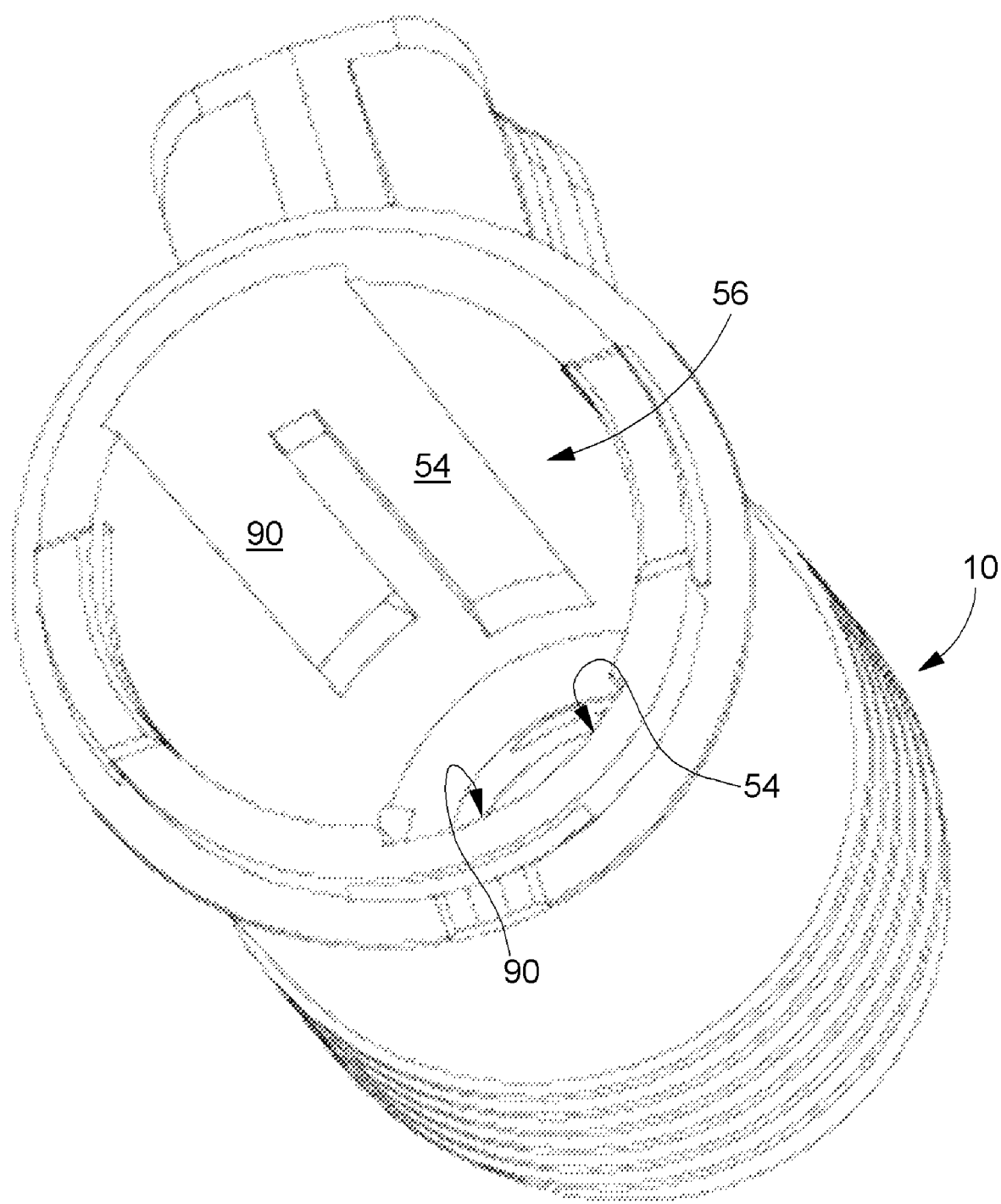
FIG. 12A is a perspective view of the main body showing the path of the cam arranged in the inner wall of said main body.

The position of secondary body 12 is indexed relative to sheath 6 via its two inclined planes 40 which have to be slid into the hollows of elastic V-shaped arms 38. As regards the position of sheath 6 relative to main body 10, this is indexed by at least one and preferably two diametrically opposite snugs 52 (see FIG. 7A) which are engaged in the longest grooves 54 of two cam paths 56 arranged in the inner lateral wall of main body 10 (see FIG. 12A).

Figure 10A:
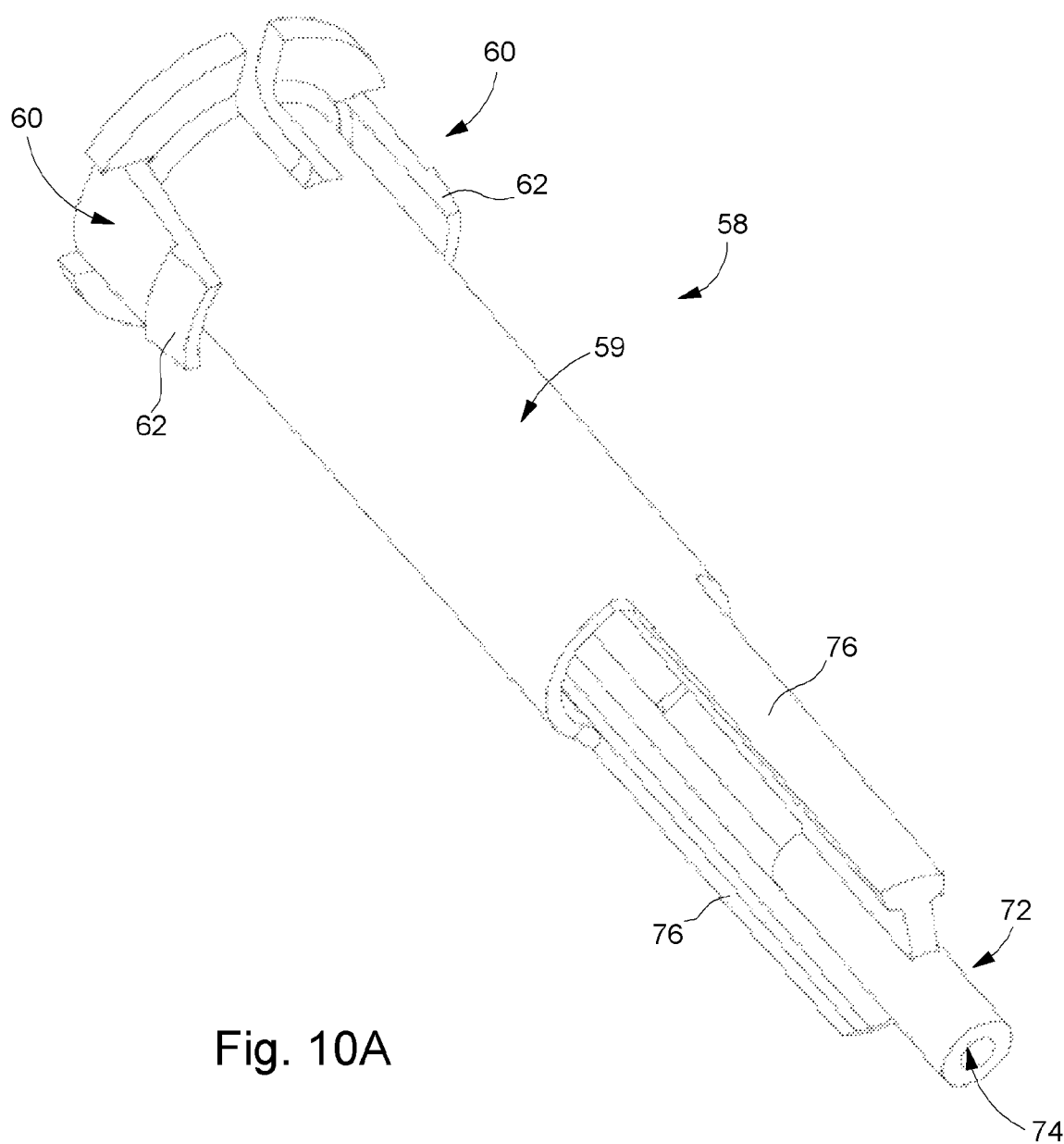
FIG. 10A is a perspective view of the base used for holding the needle according to a first embodiment.
Figure 10B:
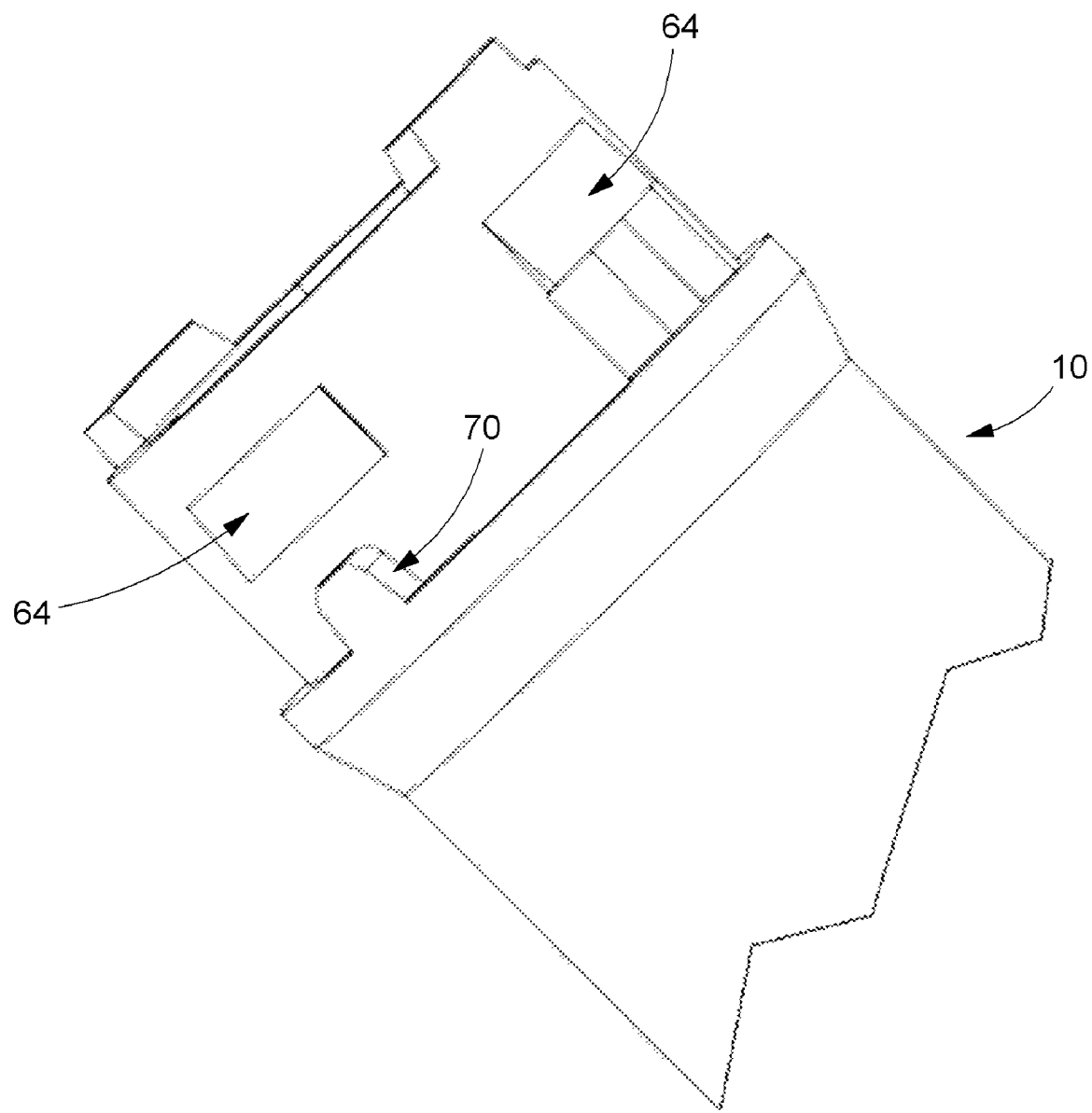
FIG. 10B is a detailed perspective view of the proximal end of the main body.
Figure 11C:
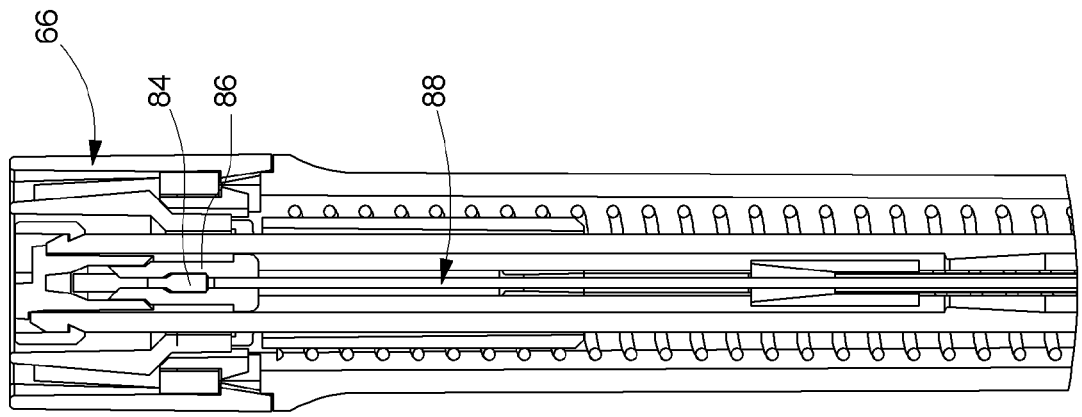
FIG. 11C is a larger scale view of the zone surrounded by a circle in FIG. 11A which shows the coupling of the head of the piston rod on the end cap.
Figure 11B:
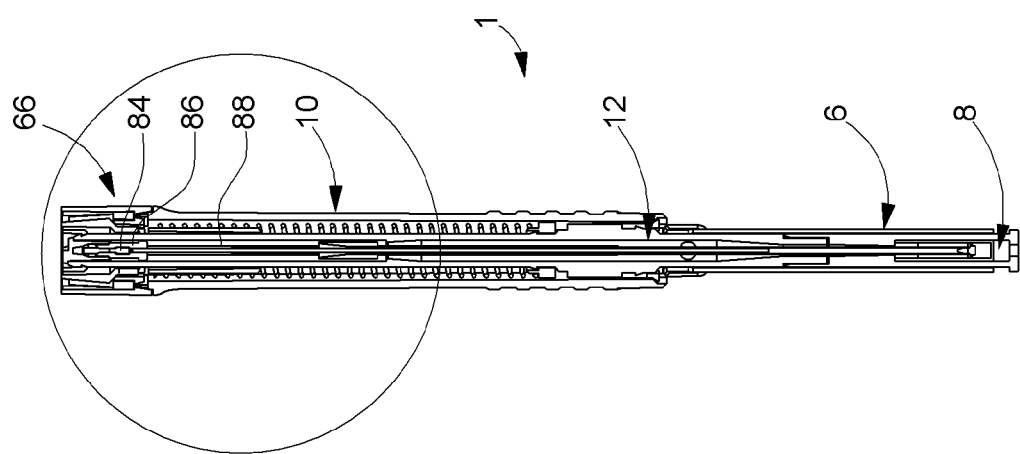
FIG. 11B is a longitudinal cross-section of the back injection device in the rest position.
Figure 11A:
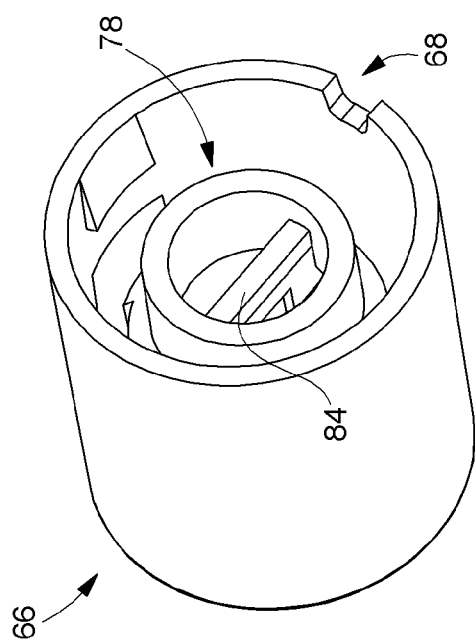
FIG. 11A is a perspective view of the end cap.

Hollow needle 28 is carried (see FIG. 10A) by a substantially cylindrical holding part called the base and designated as a whole by the general reference numeral 58. The proximal end of base 58 is cut into slots that form tongues 60 provided with raised portions at the base thereof. These raised portions 62 project into corresponding apertures 64 arranged at the proximal end of main body 10 for locking base 58 to said main body 10 (see FIG. 10B). Moreover, base 58 is capped by an end cap 66 (see FIG. 11A), which has at the base thereof a notch 68 housing an indexing portion 70 provided on main body 10.

Towards its distal end, base 58 includes a tube portion 72 which defines a through aperture 74 for holding hollow needle 28 by friction and or bonding and which is connected to hollow cylindrical body 59 of base 58 by one and preferably two diametrically opposite ribs 76.

A sleeve 78 of cylindrical shape extends coaxially inside end cap 66. As described in detail hereafter, cap 66 also includes a bar 84 which extends along a diameter inside sleeve 78 and to which there is secured by gripping the head 86 of a piston rod 88 able to slide inside hollow needle 28 to hold implant 30 in placed at the moment of back-injection (see FIG. 11C).

Figure 12B:
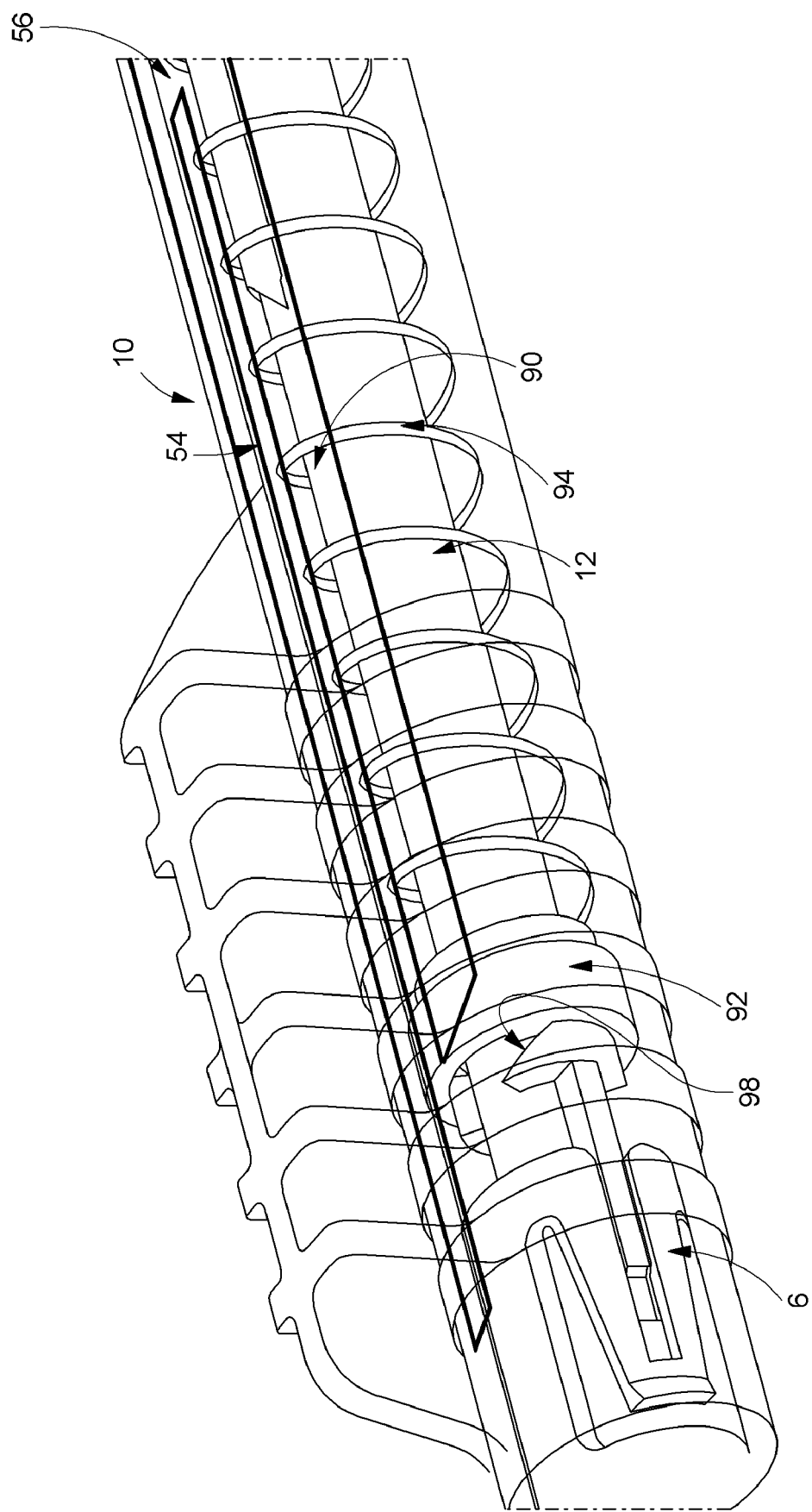
FIG. 12B is a partial perspective view of the main body in which the two longitudinal rectilinear grooves of the cam path are particularly visible.
Figure 13A:
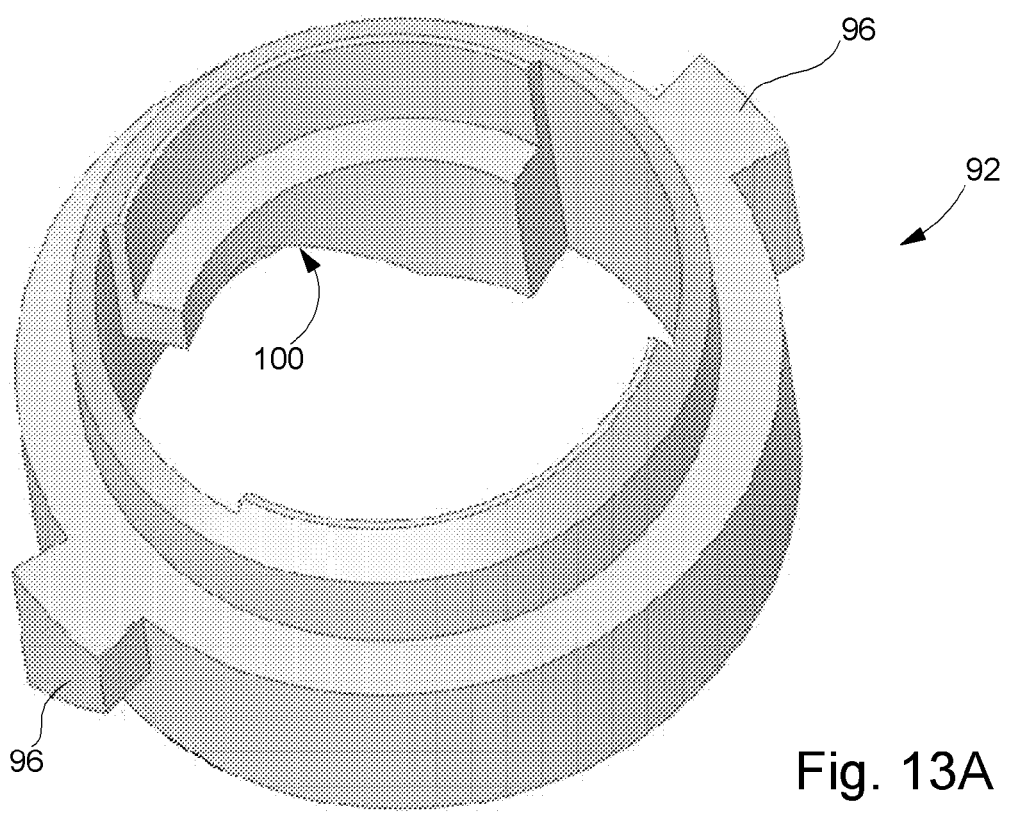
FIGS. 13A and 13B are perspective front face and back face views of the collar.
Figure 13B:
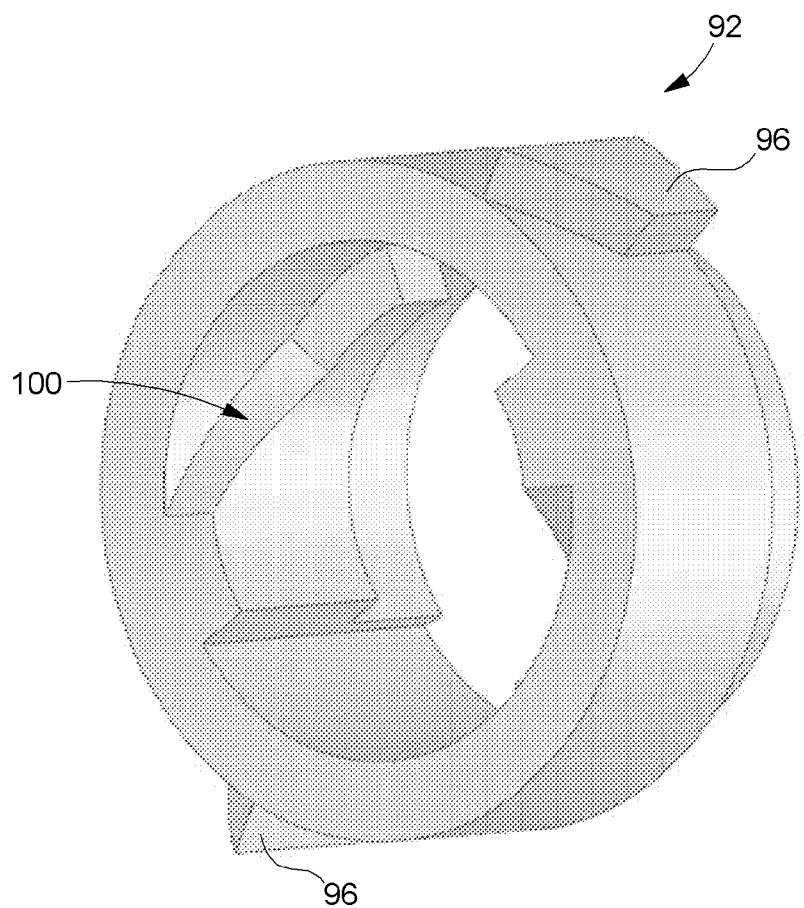
Figure 14A:
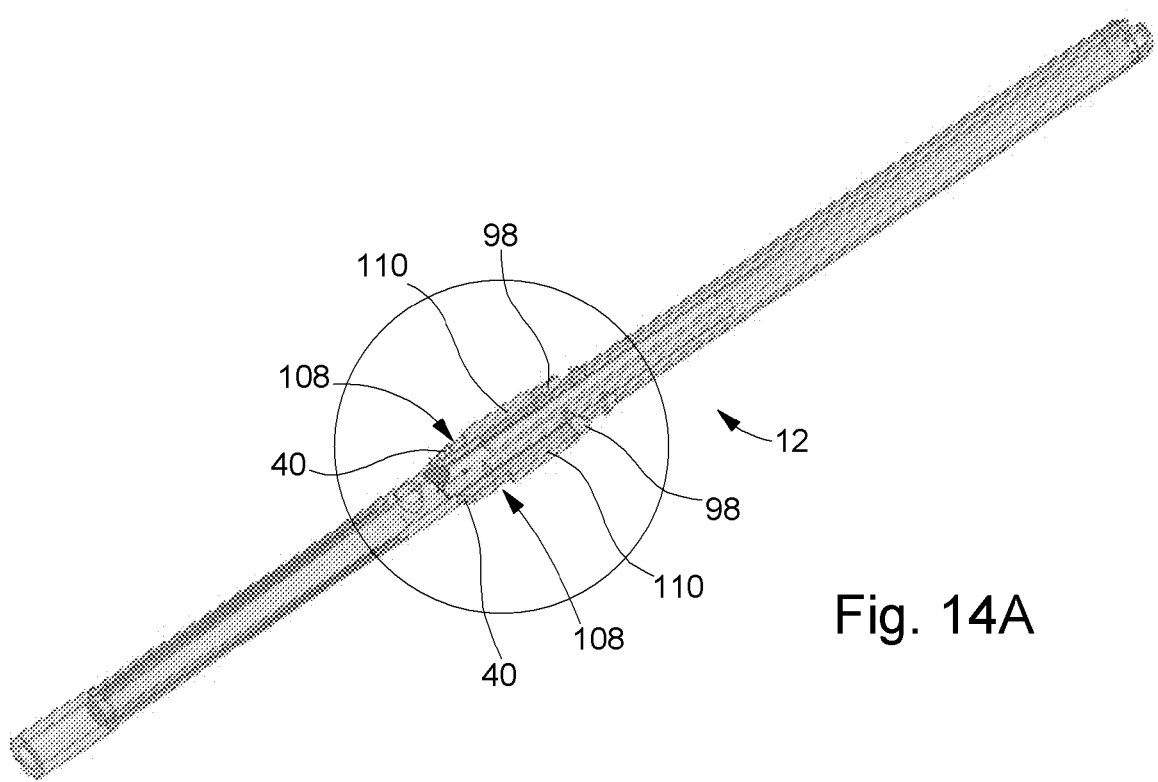
FIG. 14A is a perspective view of the secondary body according to a first embodiment.
Figure 14B:
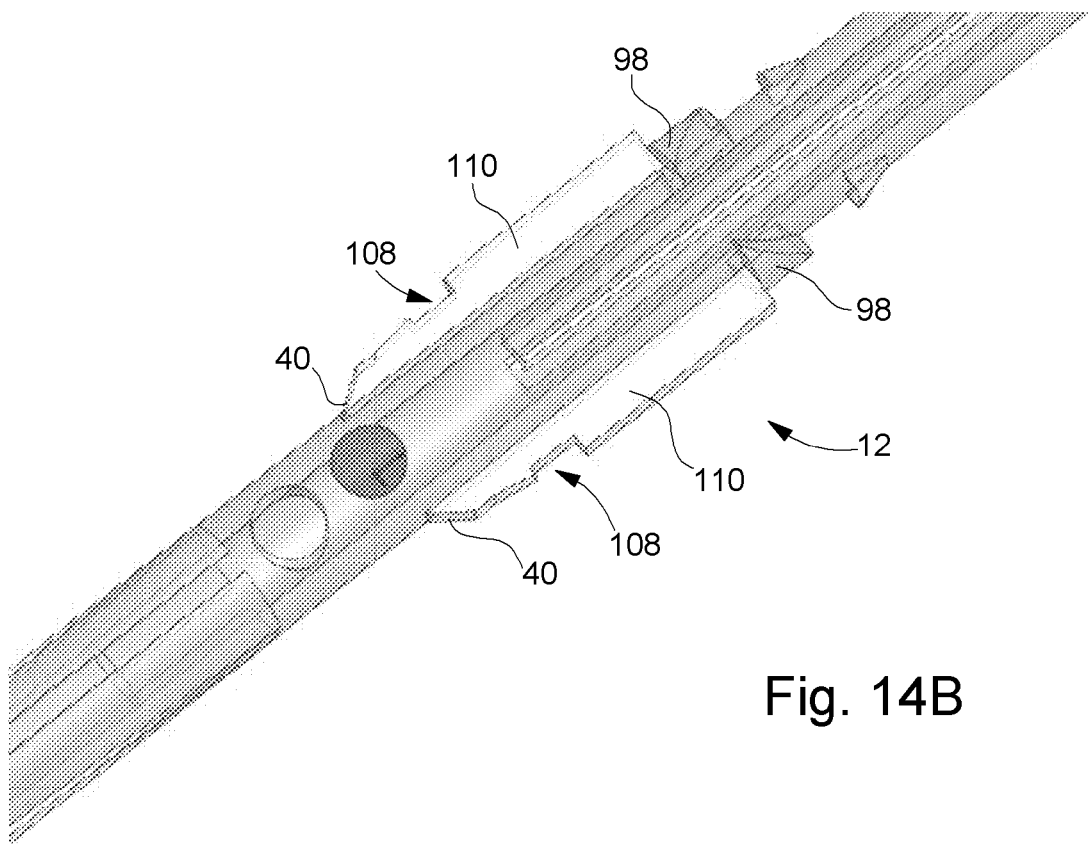
FIG. 14B is a larger scale detail view of the zone surrounded by a circle in FIG. 14A.
Figure 14C:
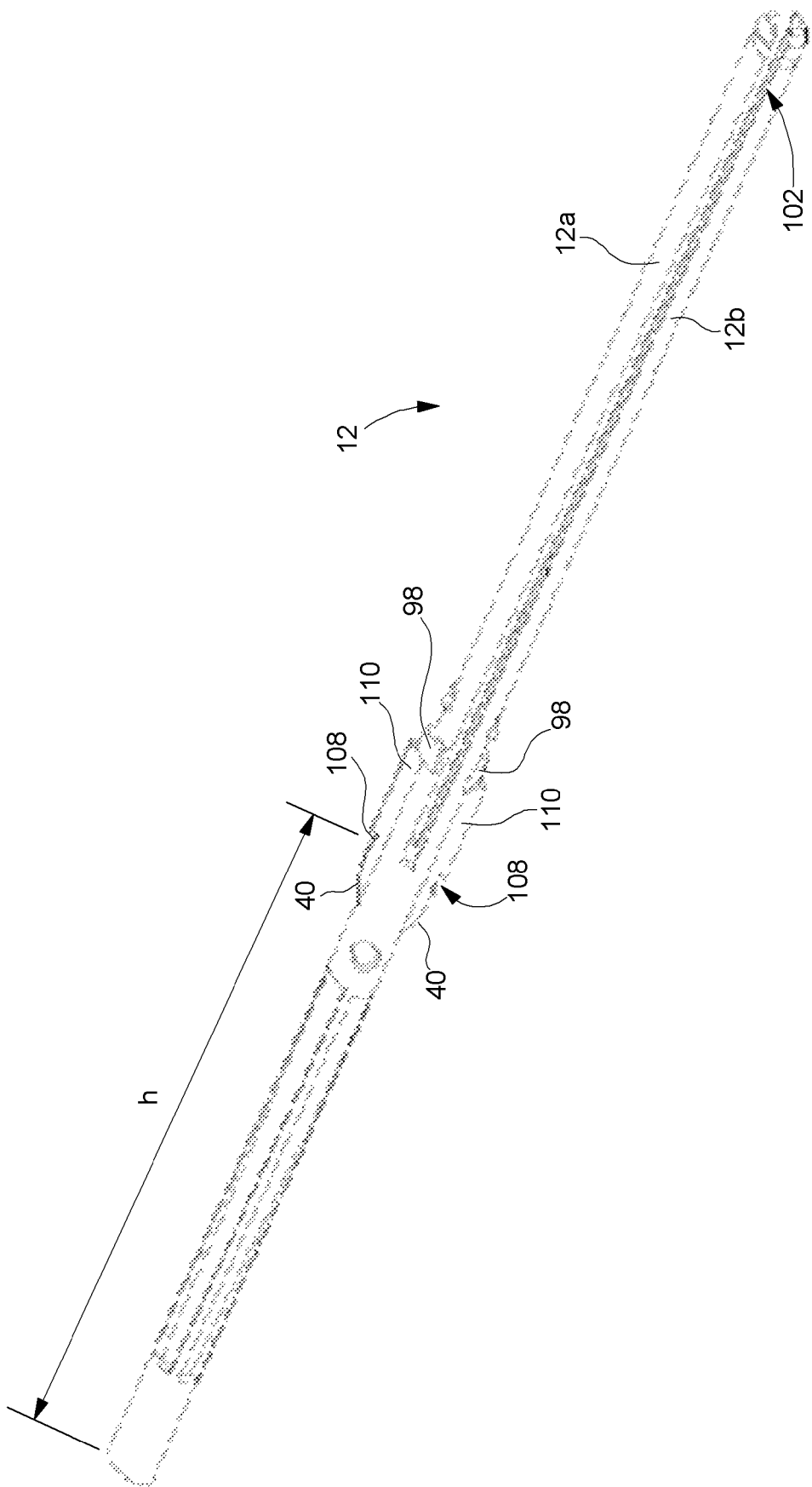
FIG. 14C is another perspective view of the secondary body in which the two tube portions are particularly visible.

As already mentioned above, main body 10 has on its inner surface at least one and preferably two diametrically opposite cam paths 56 each formed of two longitudinal rectilinear grooves 54 and 90, one 54 of which is longer than the other 90. A collar 92 is used as a support piece for a spring 94 (see FIGS. 12A and 12B). In the storage position of back-injection device 1, this spring 94 is slightly prestressed. As will be seen hereafter, this spring 94 will be compressed further as soon as said back-injection device 1 is pressed against the subject's skin 22 and will again be allowed to be let down at the moment of actual back-injection. Collar 92 is able to slide inside main body 10 and for this purpose has at its periphery two diametrically opposite snugs 96 which are capable of each cooperating with one or other of the two grooves 54, 90 of the cam paths 56 as a function of the angular position of said collar 92 inside said main body 10 (see FIGS. 13A and 13B). This position is controlled by secondary body 12 which has a cam surface 98 for this purpose (see FIGS. 14A to 14C) against which collar 92 abuts via a cam path 100 arranged in its inner surface. When snugs 96 carried by collar 92 exit the shortest grooves 90, said collar 92, constrained by spring 94, slides via its cam path 100 along the cam surface 98 of secondary body 12, which forces it to pivot, its snugs 96 then penetrating the longest grooves 54 allowing spring 94 to be let down again.

Figure 15:
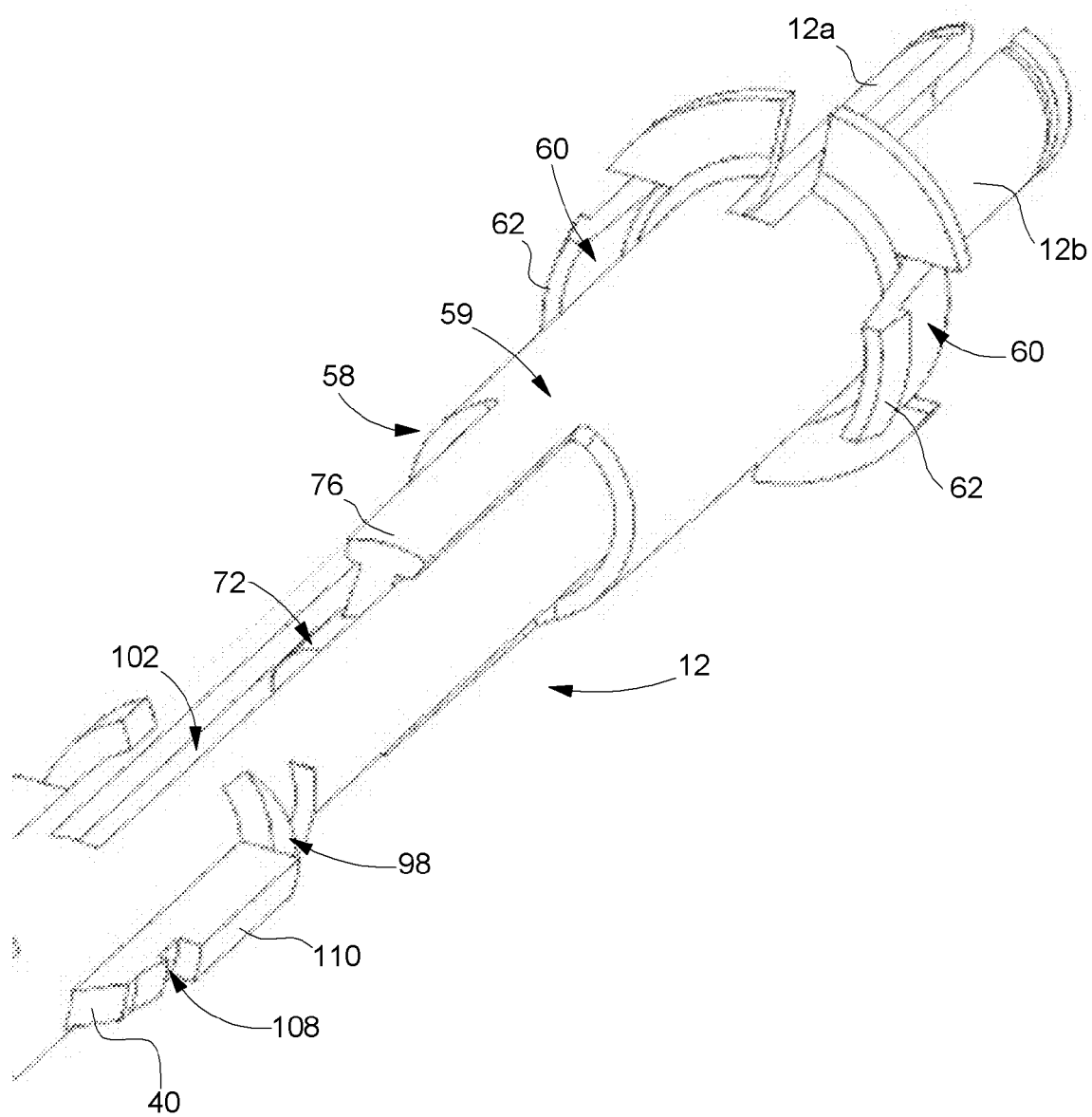
FIG. 15 is a partial perspective view showing the secondary body engaged in the base of the needle.

Secondary body 12 is a hollow body of generally cylindrical shape provided with two rectilinear diametrically opposite slots 102 which extend from the proximal end of said secondary body 12 to a height h above distant end 4 of back-injection device 1. As will be seen hereafter, this height h determines the depth of penetration of hollow needle 28 into the subject's skin 22. Indeed, slots 102 define two tube portions 12a and 12b which pass right through tube portion 72 in which hollow needle 28 is fixed and which penetrate the interior of hollow cylindrical body 59 of base 58 (see FIG. 15). Thus, this base 58 is free to slide along secondary body 12 until ribs 76, via which tube portion 72 is connected to body 59 of said base 58, is stopped at the bottom of slots 102. Moreover, the two tube portions 12a, 12b pass on either sides of bar 84 and penetrate the interior of sleeve 78 which they exit via proximal end 103 of back-injection device 1. The two tube portions 12a, 12b of secondary body 12 are thus capable of gradually emerging from main body 10 as hollow needle 28 penetrates the subject's skin 22.

Figure 16A:
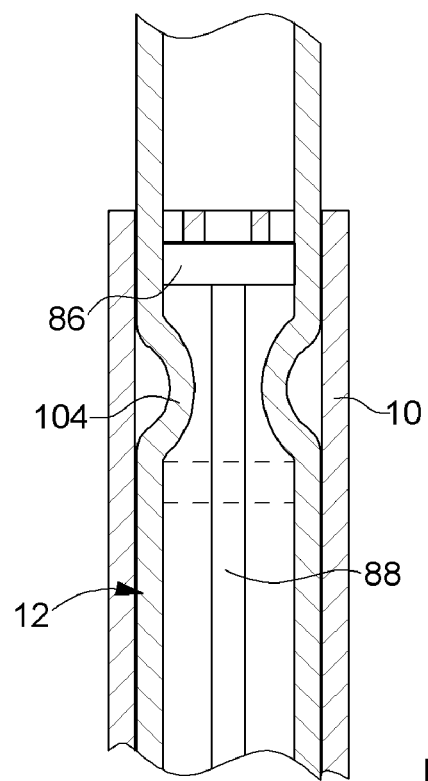
FIGS. 16A and 16B are schematic views shown in the cooperation between the piston rod head and the locking means provided on the secondary body.
Figure 16B:
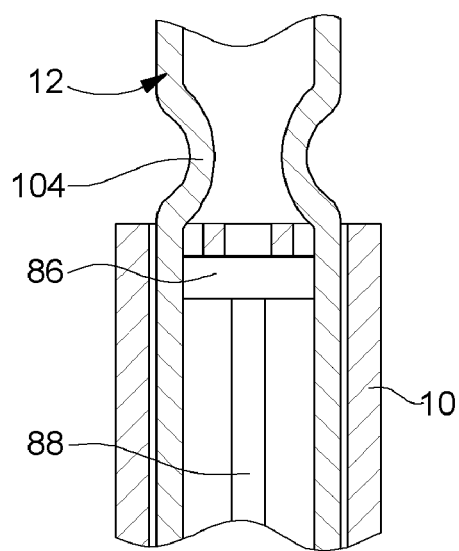
Figure 18A:
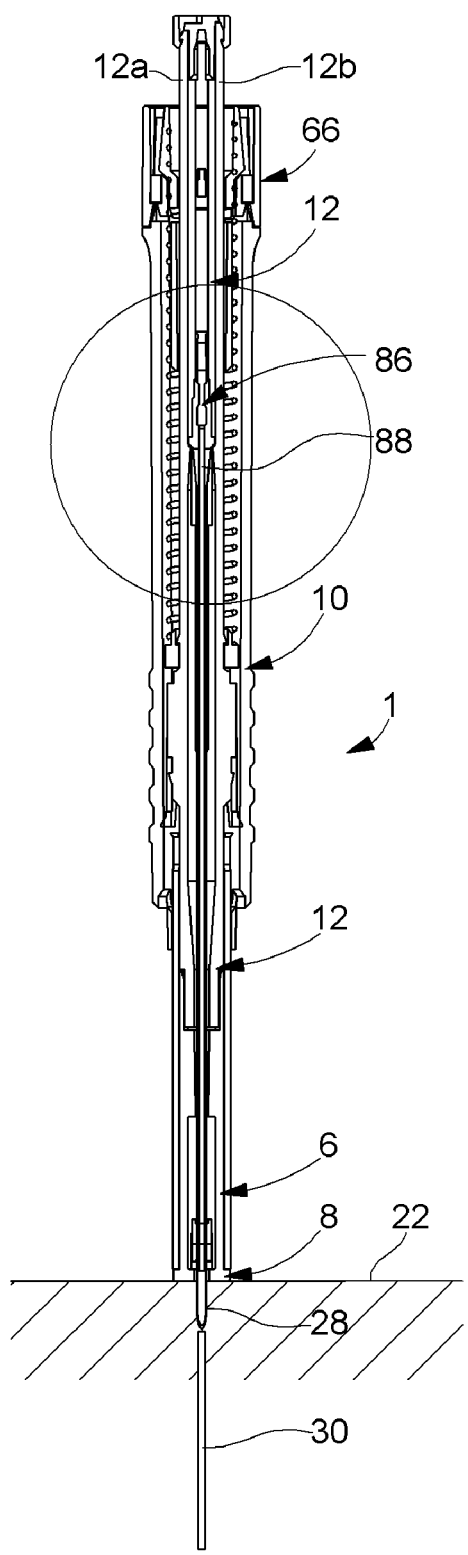
FIG. 18A is a longitudinal cross-section of the back injection device during the phase of injecting the implant into the subject's tissue.
Figure 18B:
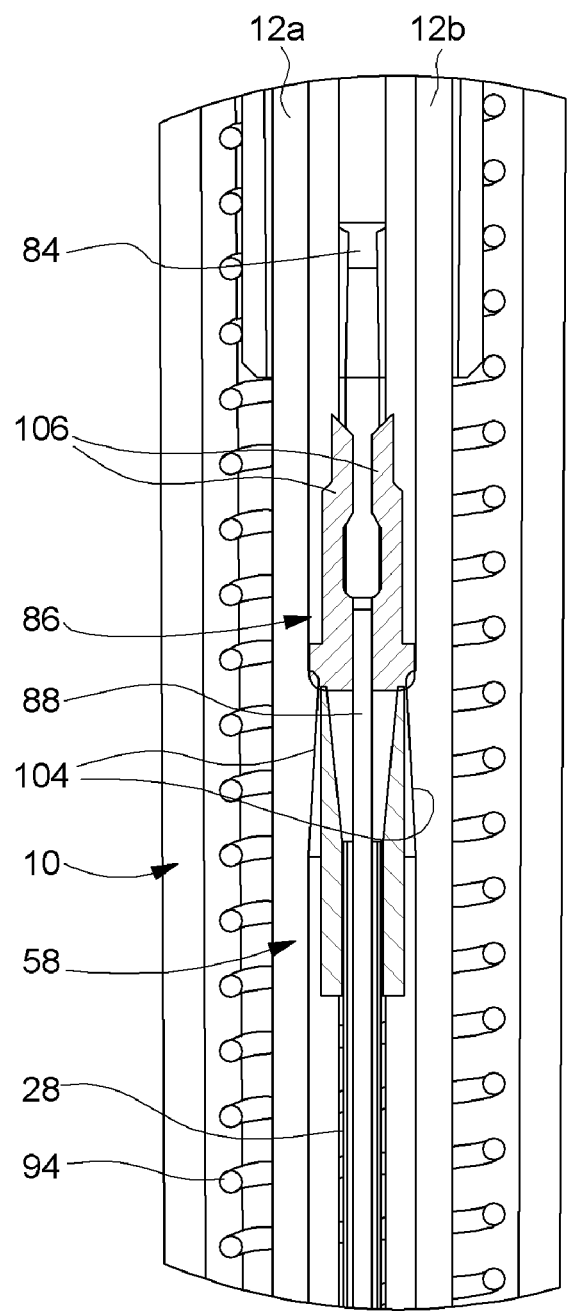
FIG. 18B is a larger scale detail view of the zone surrounded by a circle in FIG. 18A, the piston rod head being uncoupled from the secondary body.
Figure 19A:
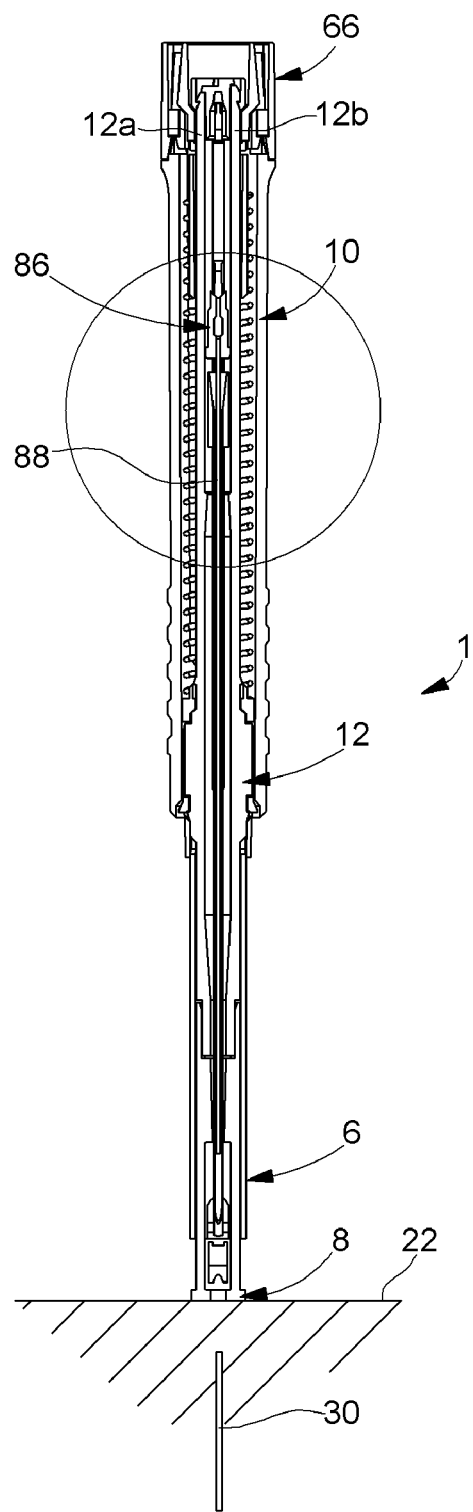
FIG. 19A is a longitudinal cross-section of the back injection device after complete withdrawal of the needle from the subject's tissue.
Figure 19B:
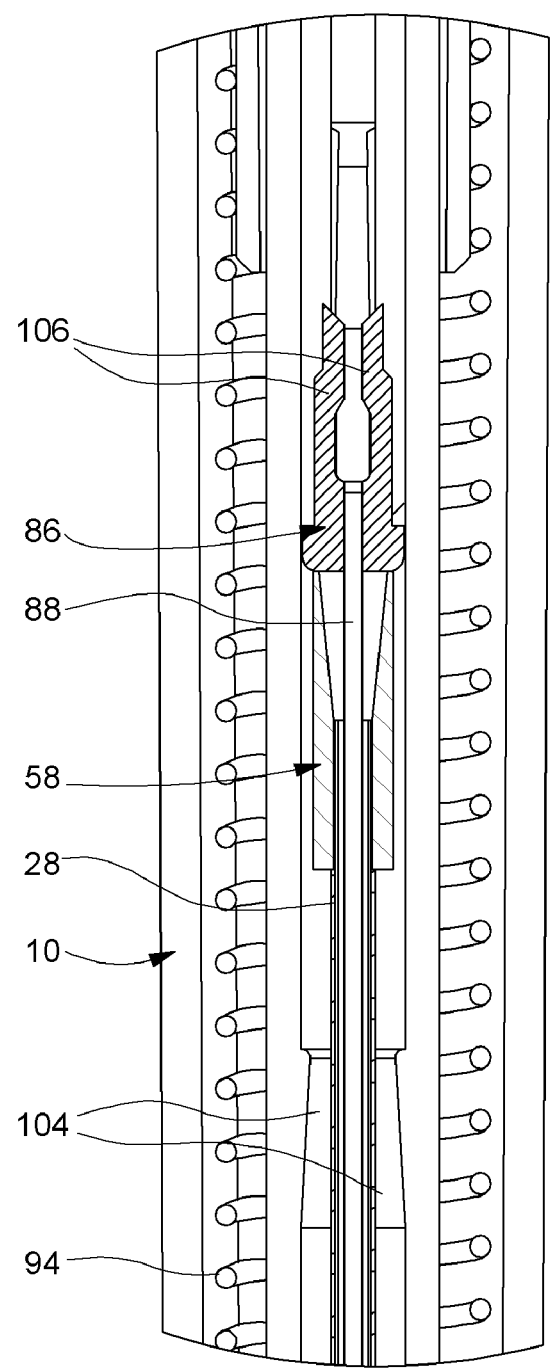
FIG. 19B is larger scale detail view of the zone surrounded by a circle in FIG. 19A, the piston rod head again being coupled to the main body.

Finally, secondary body 12 includes on the inner face of the two tube portions 12a, 12b locking means 104, for example in the form of two beads (see FIGS. 16A and 16B). For a detailed description of these locking means 104, reference can usefully be made to European Patent Application No. 04028413.5 in the name of the Applicant. The function of locking means 104 is to uncouple head 86 of piston rod 88 from main body 10 and to couple it to secondary body 12. Indeed, after use, head 86 of piston rod 88 is gripped by two elastic clips 106 on bar 84, which extends diametrically inside sleeve 78 of end cap 66. Gradually as hollow needle 28 penetrates the subject's skin 22, the two tube portions 12a, 12b of secondary body 12 emerge from main body 10, such that the two beads 104 meet head 86 of piston rod 88 and end up passing behind the latter by deforming elastically (see FIGS. 17A and 17B). During the actual back injection operation, the progressive withdrawal of hollow needle 28 out of the subject's skin 2 is controlled. Piston rod 88 does not however accompany this movement of withdrawal (see FIGS. 18A and 18B). Indeed, since beads 104 retain its head 86, it is uncoupled from main body 10 (more specifically from end cap 66) and remains immobile, thus gradually penetrating hollow needle 28 as the latter exits the subject's skin 22. Implant 30 thus emerges from needle 28, held in position at the correct depth in skin 22 by the distal end of piston rod 88, which is abutting against said implant 30. During the downward movement of secondary body 12 relative to main body 10, the proximal end of base 58 meets head 86 of piston rod 88. As during the upward movement of secondary body 12 inside main body 10, locking means 104 carried by secondary body 12 will pass by head 86 of piston rod 88 by deforming elastically, thereby uncoupling head 86 of piston rod 88 from secondary body 12 and coupling it again to main body 10 in order to allow the downward movement of secondary body 12 to continue and thereby allow the latter to cover needle 28 and piston rod 88 (see FIGS. 19A and 19B).

Figure 20A:
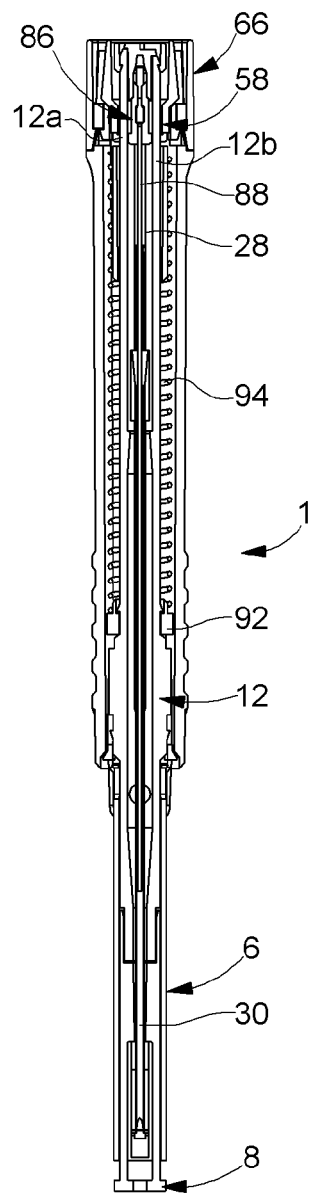
FIGS. 20A, 20B and 20C are longitudinal cross-sections of the back injection device respectively prior to use, at the moment when the needles reaches maximum penetration in the subject's skin, and after final locking and which illustrate the cooperation between the spring and the collar.
Figure 20B:
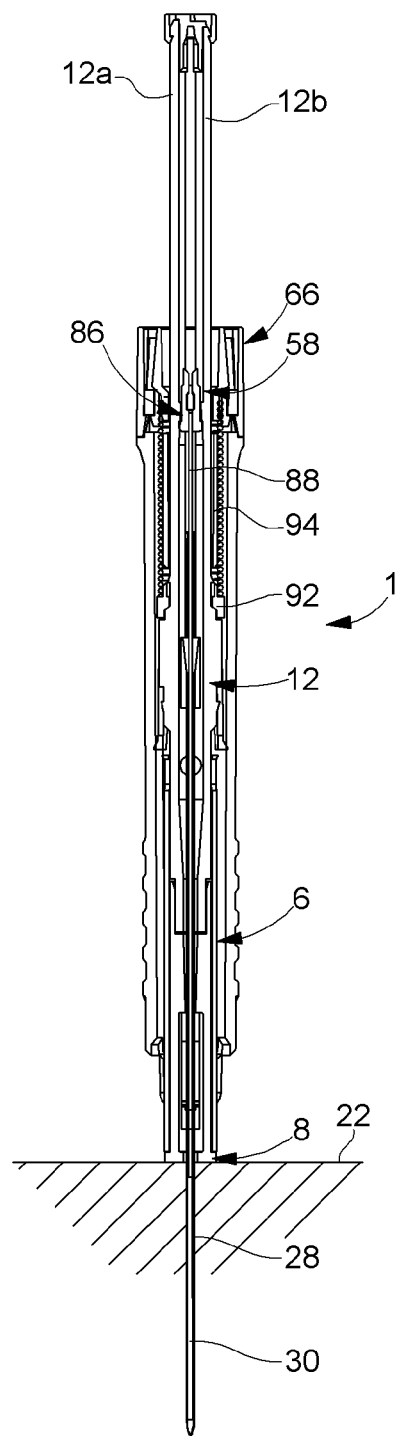
Figure 20C:
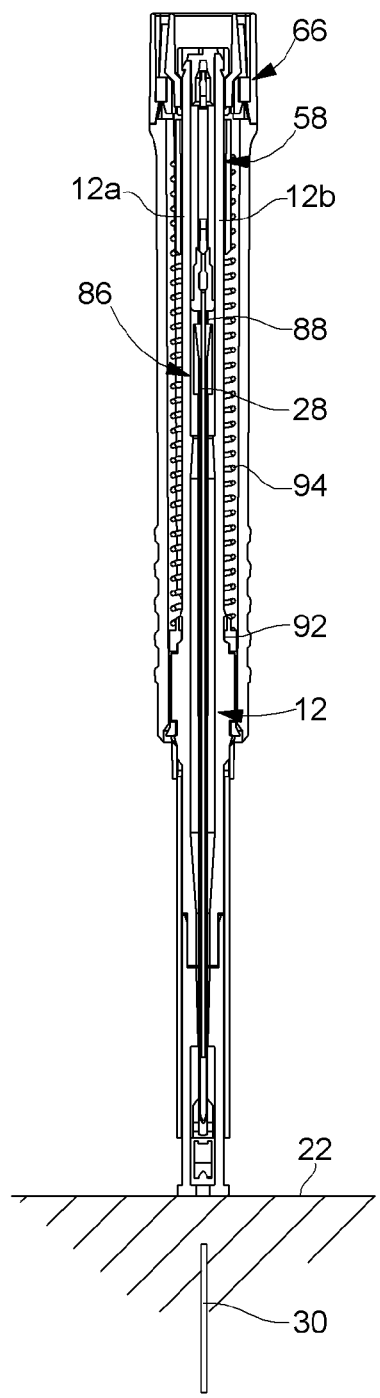
Figure 21A:
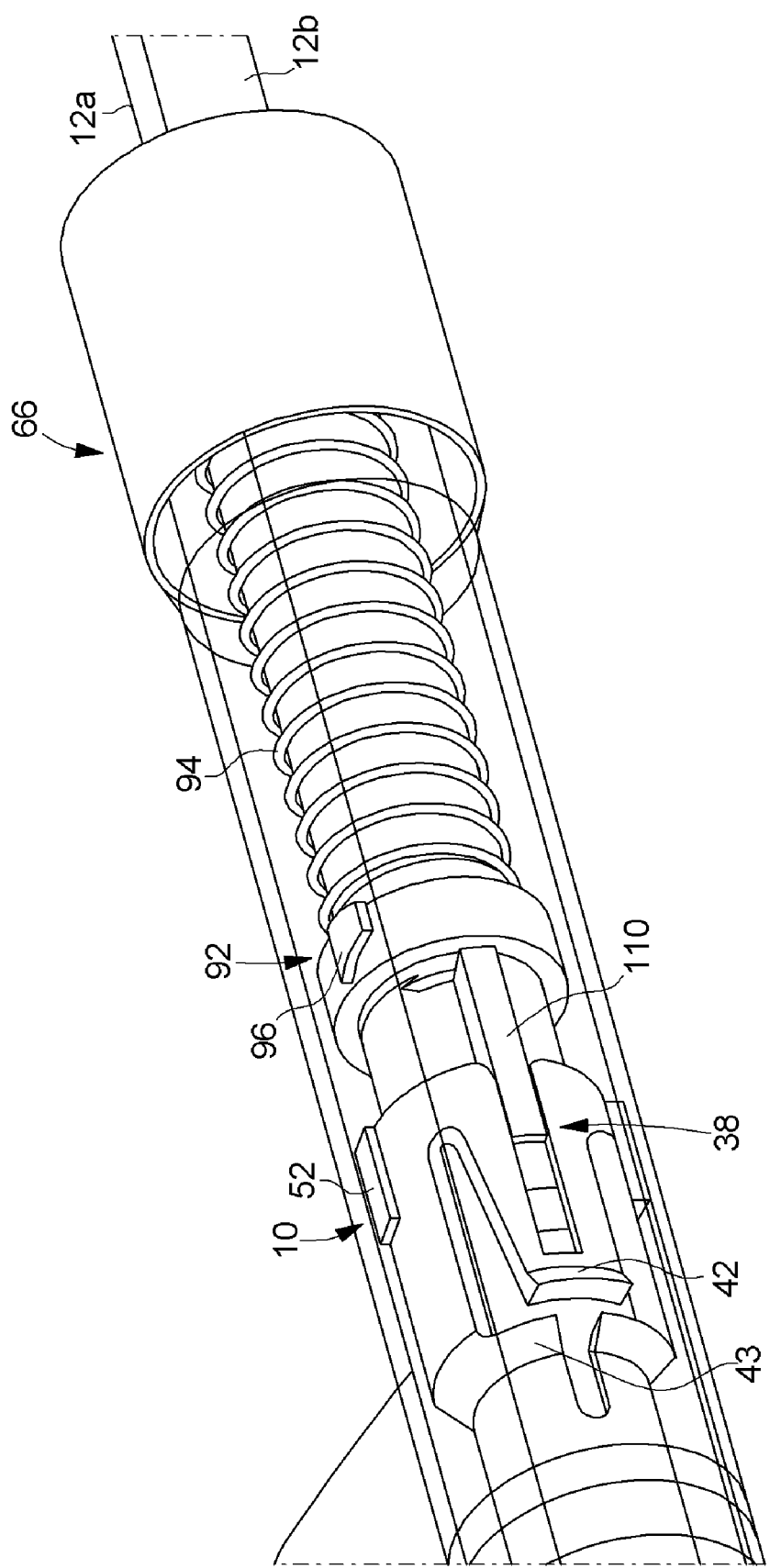
FIG. 21A is a partial perspective view of the back injection device showing the collar just prior to pivoting.
Figure 21B:
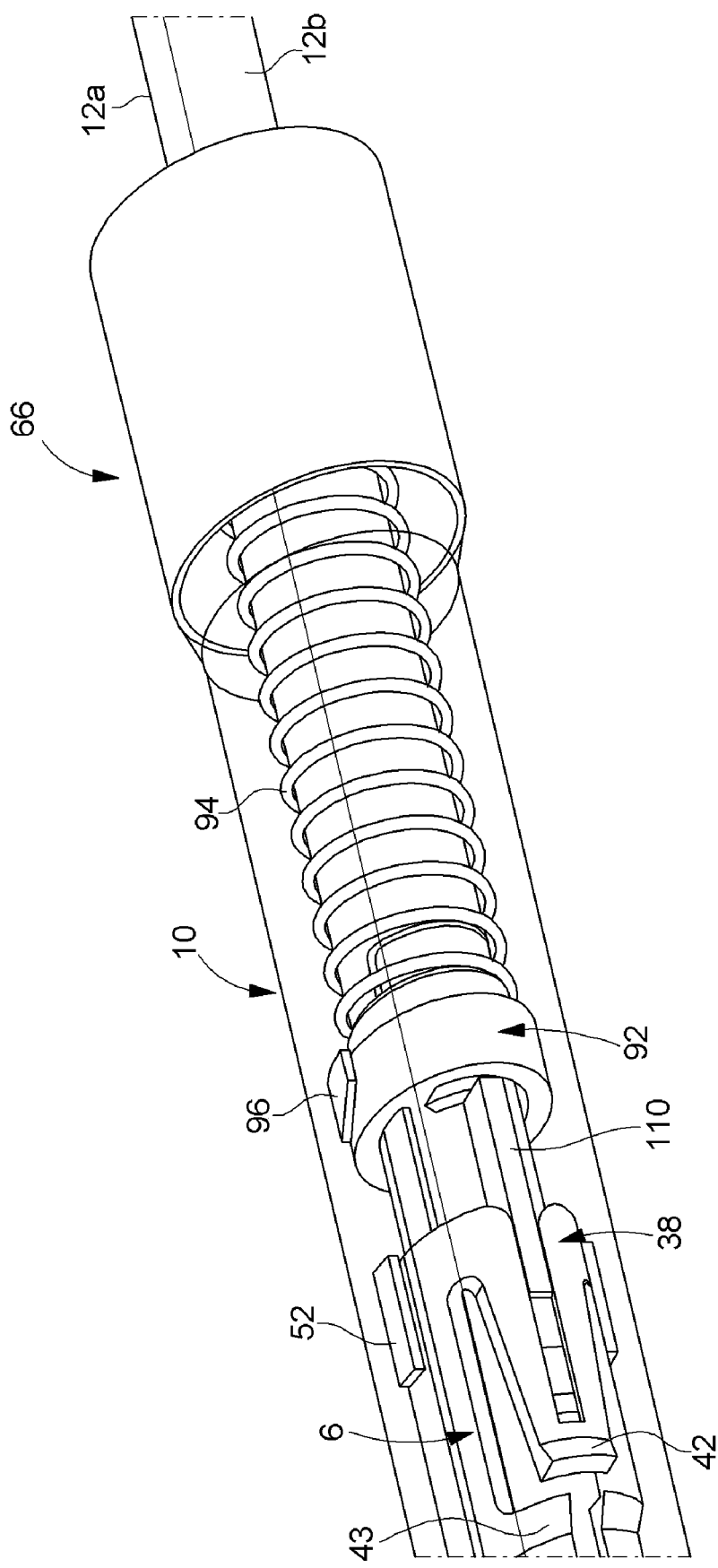
FIG. 21B is a similar view to that of FIG. 21A showing the collar after pivoting.
Figure 21C:
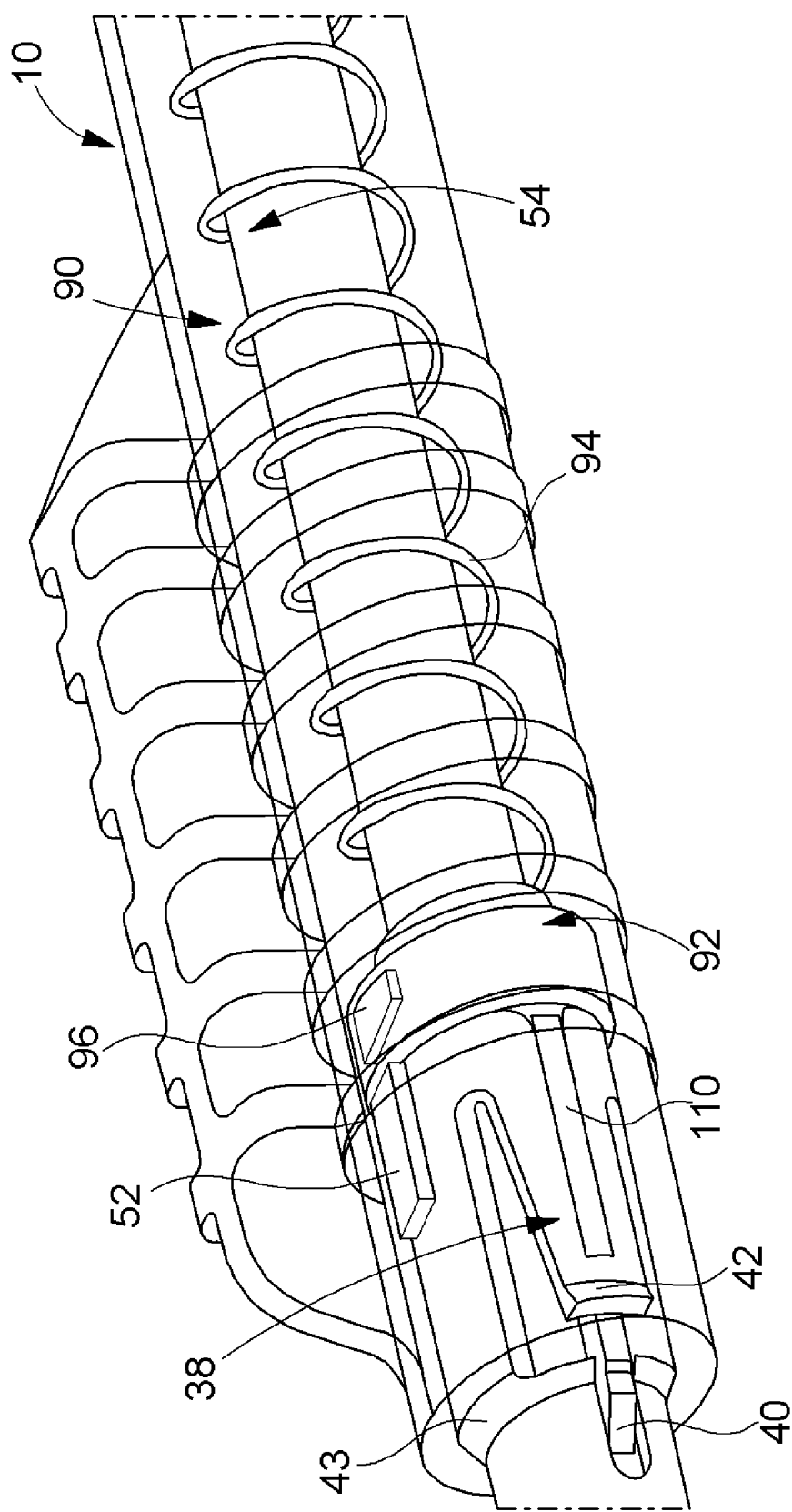
FIG. 21C is a partial perspective view showing the collar stopped at the bottom of the longest grooves of the cam path arranged in the inner wall of the main body.
Figure 22C:
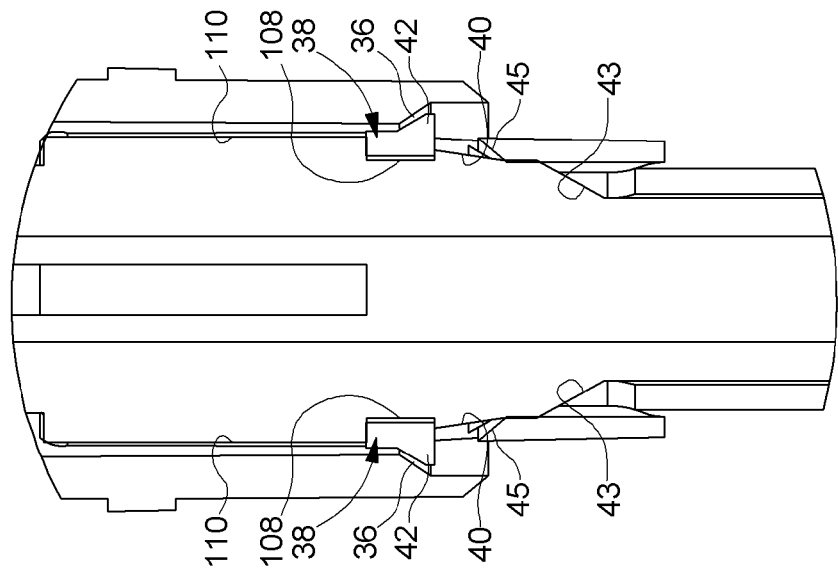
FIG. 22C is a larger scale detail view of the zone surrounded by a circle in FIG. 22A, which shows the secondary body locked onto the sheath, which is itself locked onto the main body.
Figure 22B:
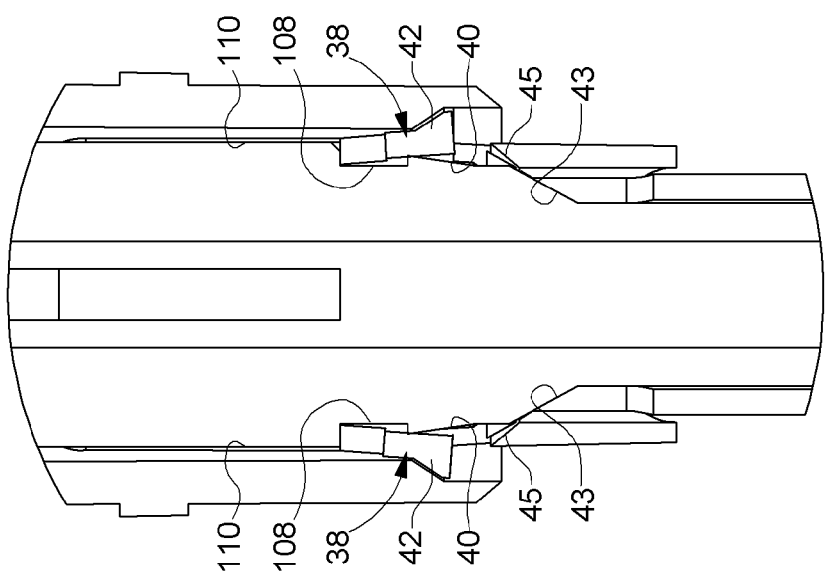
FIG. 22B is a larger scale detail view of the zone surrounded by a circle in FIG. 22A, which shows the secondary body just prior to being locked onto the sheath.
Figure 22A:
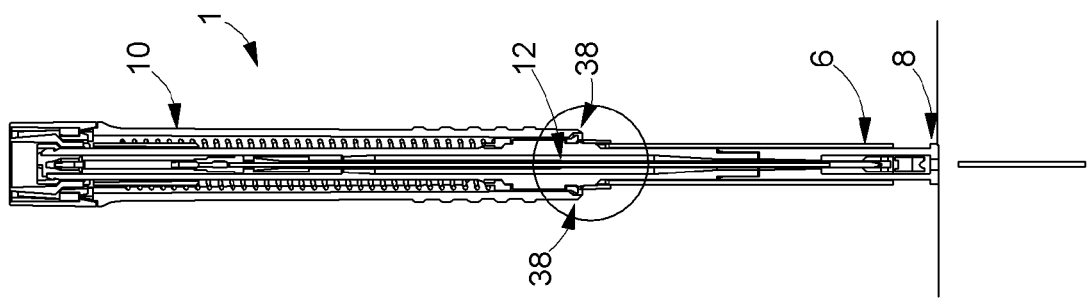
FIG. 22A is a longitudinal cross-section of the back injection device after injection of the implant into the subject's skin.

As illustrated in FIGS. 20A to 20C, spring 94 is stopped at the distal end thereof against collar 92 and at the proximal end thereof against base 58. Gradually as sheath 6 retracts inside main body 10 when back-injection device 1 is pressed against the subject's skin 22, secondary body 12 drives with it collar 92, which abuts via its cam path 100 against the cam surface 98 of said secondary body 12. During this movement of translation, snugs 96 of collar 92 slide along the shortest grooves 90 of the two cam paths 56 arranged in the inner wall of main body 10. Once it reaches the return point, defined by the place where the shortest grooves 90 communicate with the longest grooves 54 (see FIG. 21A), collar 92, which is no longer being guided axially, pivots while following via its cam path 100 the cam surface 98 arranged on secondary body 12 (see FIG. 21B). This event is concomitant with the passage of locking means 104 of secondary body 12 behind head 86 of piston rod 88. At this moment, snugs 96 of collar 92 penetrate the longest grooves 54 of cam paths 56, allowing spring 94 to be let down again (see FIG. 21C). By letting down, spring 94 pushes secondary body 12 forward, in the direction of exit from main body 10. The thrust force of spring 94 is transmitted to secondary body 12 via collar 92. Simultaneously, secondary body 12 pushes forward sheath 6 in the direction of exit from main body 10. Secondary body 12 transmits it thrust force to sheath 6 via its inclined planes 40, which abut against the bottom of the V-shaped elastic arms 38. In fact, these arms, abutting against the inner wall of main body 10, are not allowed to move apart. The exit movement of sheath 6 out of main body 10 is interrupted when said sheath 6 abuts via its truncated edges 43 against inner shoulder 45 provided at the distal end of main body 10. In this position, snugs 42 of elastic arms 38 are facing housing 36, such that said arms 38 are again allowed to deform elastically towards the outside of the volume of main body 10 (see FIG. 22B). This allows the corresponding inclined planes 40 arranged on secondary body 12 to slide under elastic arms 38. It will be noted that, since longitudinal grooves 54 of cam paths 56 are longer than the grooves 90 in which snugs 96 of collar 92 move, when hollow needle 28 is pushed into the subject's skin 22, at the moment when the back-injection occurs and when secondary body 12 again emerges from main body 10, said secondary body 12 is allowed to move slightly beyond the position which it has initially before injection device 1 was pressed against skin 22. Advantage is taken of this additional movement in order to make the base of V-shaped elastic arms 38 fall into two diametrically opposite slots 108 located between the feet of inclined planes 40 and two longitudinal edges 110 (see FIG. 22C). Consequently, secondary body 12 is locked onto sheath 6 which is itself locked onto main body 10, such that back-injection device 1 according to the invention is totally locked after use.

Figures 23A, 23B, 23C, 23D, 23E, 23F, 23G:
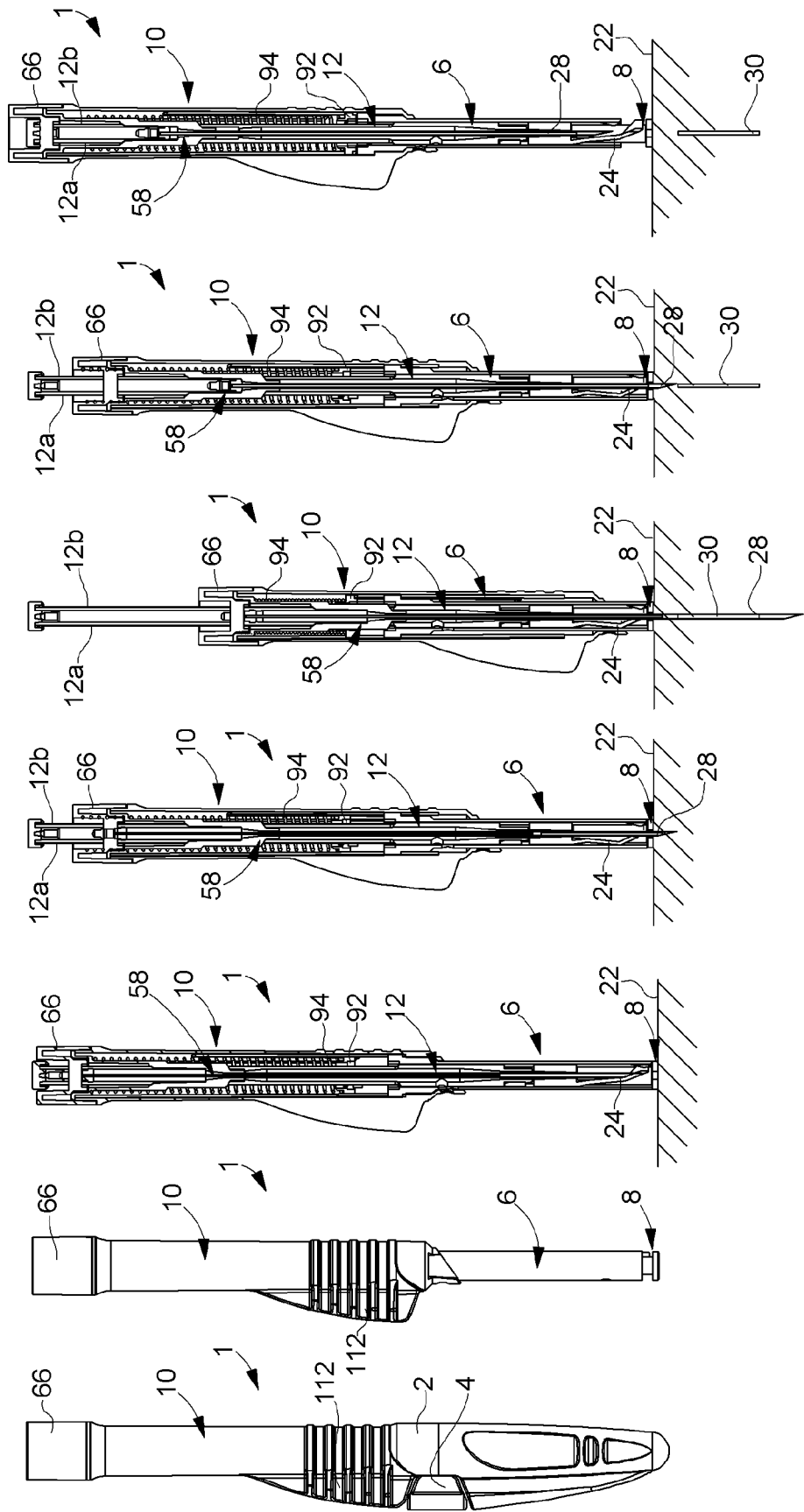
FIGS. 23A to 23G illustrate the various operating phases of the back injection device according to the invention.

We will now consider the operation of back-injection device 1 according to the invention with reference to FIGS. 23A to 23G. After having removed the device from its packaging (FIG. 23A) cap 2 is first removed then staple shaped member 14 (FIG. 23B). Back injection device 1 is then ready for use. While holding device 1 by its main body 10, it is applied against subject's skin (FIG. 23c). The presence of a corrugated rib 112 that extends over one part of the length of back-injection device 1 ensures that the latter is held firmly. Retaining element 8 is pressed against the subject's skin 22. The effect of this pressing is that retaining element 8 penetrates slightly the interior of sheath 6, which has the effect of moving elastic tongue 24 away from its rest position and freeing the passage for hollow needle 28.

Simultaneously, retaining element 8 pushes secondary body 12, to which it is secured, backwards, which moves inclined planes 40, arranged on secondary body 12, to move away from elastic arms 38, which are then able to bend. Subsequently, snugs 42 provided at the base of elastic arms 38 are released from their position engaged in housings 36 provided at the distal end of main body 10, such that sheath 6 is uncoupled from said main body 10. Retaining element 8 continues to penetrate the interior of sheath 6 until it is stopped against the distal end thereof. Retaining element 8 then exerts a thrust on sheath 6 on the one hand, and on secondary body 12 on the other hand, such that these two parts start to retract inside main body 10. It will be noted that during this movement, the relative position of sheath 6 in relation to secondary body 12 remains unchanged. As sheath 6 and secondary body 12 retract, hollow needle 28 gradually emerges from main body 10 and penetrates the subject's skin 22 (FIG. 23D). The movement of withdrawal of secondary body 12 is allowed because the two tube portions 12a, 12b of which it is formed exit via the proximal end of back-injection device 1 by sliding inside sleeve 78, passing right through bar 84, which extends radially inside said sleeve 78 (FIG. 23E)

By moving up inside main body 10, secondary body 12 meets head 86 of piston rod 88, which is held initially coupled to main body 10 via its two elastic clips 106 clamped onto bar 84 of sleeve 78. The two beads 104 arranged on the inner face of tube portions 12a, 12b thus reach the height of head 86 of piston rod 88 and pass behind the latter by deforming elastically. In parallel, secondary body 12 drives with it collar 92, which slides via its snugs 96 along the shortest grooves 90 of cam paths 56 arranged diametrically opposite each other in the inner wall of said main body 10. Spring 94, abutting against collar 92, which moves up inside main body 10 and against base 58 which is fixed, is compressed.

When collar 92 reaches the point of return where the shortest grooves 90 communicate with the longest grooves 54 of cam paths 56, the two beads 104 pass right through head 86 of piston rod 88. Moreover, said collar 92 which, at that moment, is no longer guided axially, is forced to pivot via the effect of the pressure exerted by spring 94 and is engaged via its snugs 96 in the longest grooves 56. At that moment, spring 94 is again allowed to be let down and pushes secondary body 12 forward, which itself exerts a thrust on sheath 8 in the direction of exit from main body 10 (FIG. 23F). During the exit movement of secondary body 12, beads 104 retain head 86 of piston rod 88, which uncouples from main body 10 and is again coupled to secondary body 12. Piston rod 88 thus remains immobile, gradually penetrating hollow needle 28 to hold implant 30 in position at the correct depth in the subject's skin 22.

The forward movement of sheath 6 is interrupted when the latter is stopped via its two truncated edges 43 against the inner shoulder 45 provided at the distal end of main body 10. Simultaneously, secondary body 12 slides via its inclined planes 40 under elastic arms 38. The latter are housed in two the two slots 108 provided behind said inclined planes 40. Secondary body 12 is thus locked onto sheath 6 which is itself locked onto main body 10 via its elastic arms 38, whose snugs 42 engage in housings 36 of main body 10. The back-injection device 1 according to the invention is thus totally and irreversibly locked (FIG. 23G).

Figure 24A:
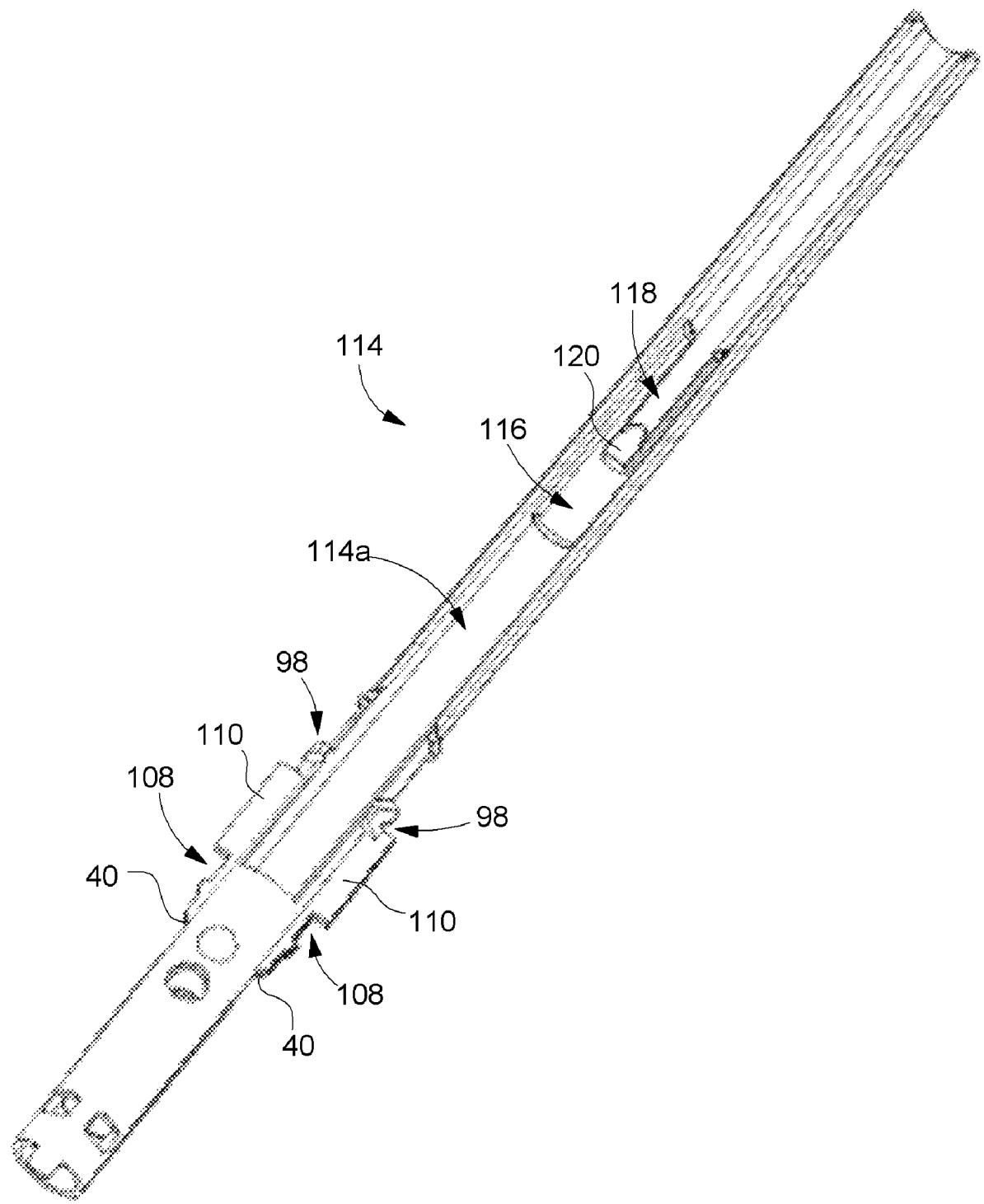
FIG. 24A is a perspective and top view of the secondary body according to a second embodiment.
Figure 24B:
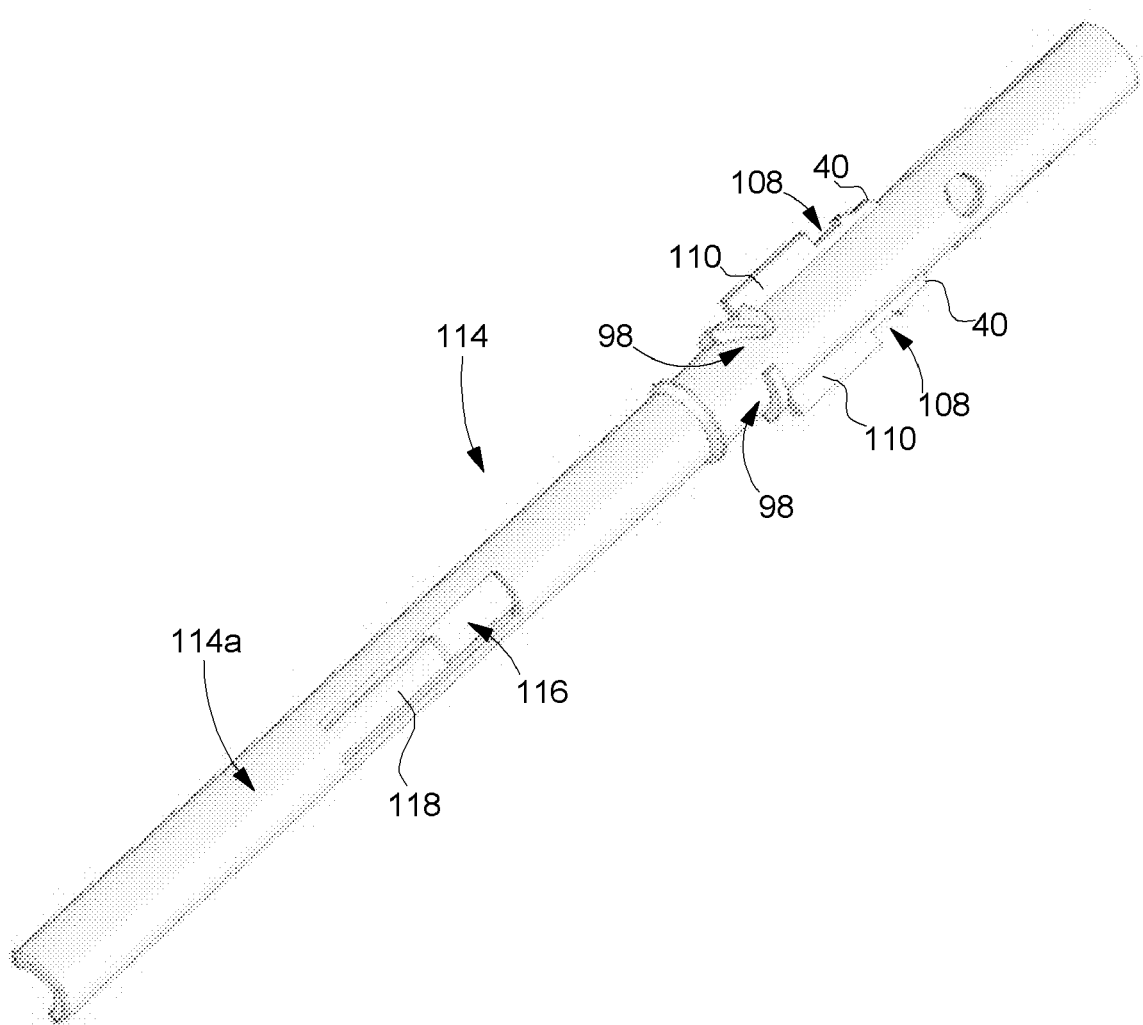
FIG. 24B is a perspective and bottom view of the secondary body shown in FIG. 24A.
Figure 25A:
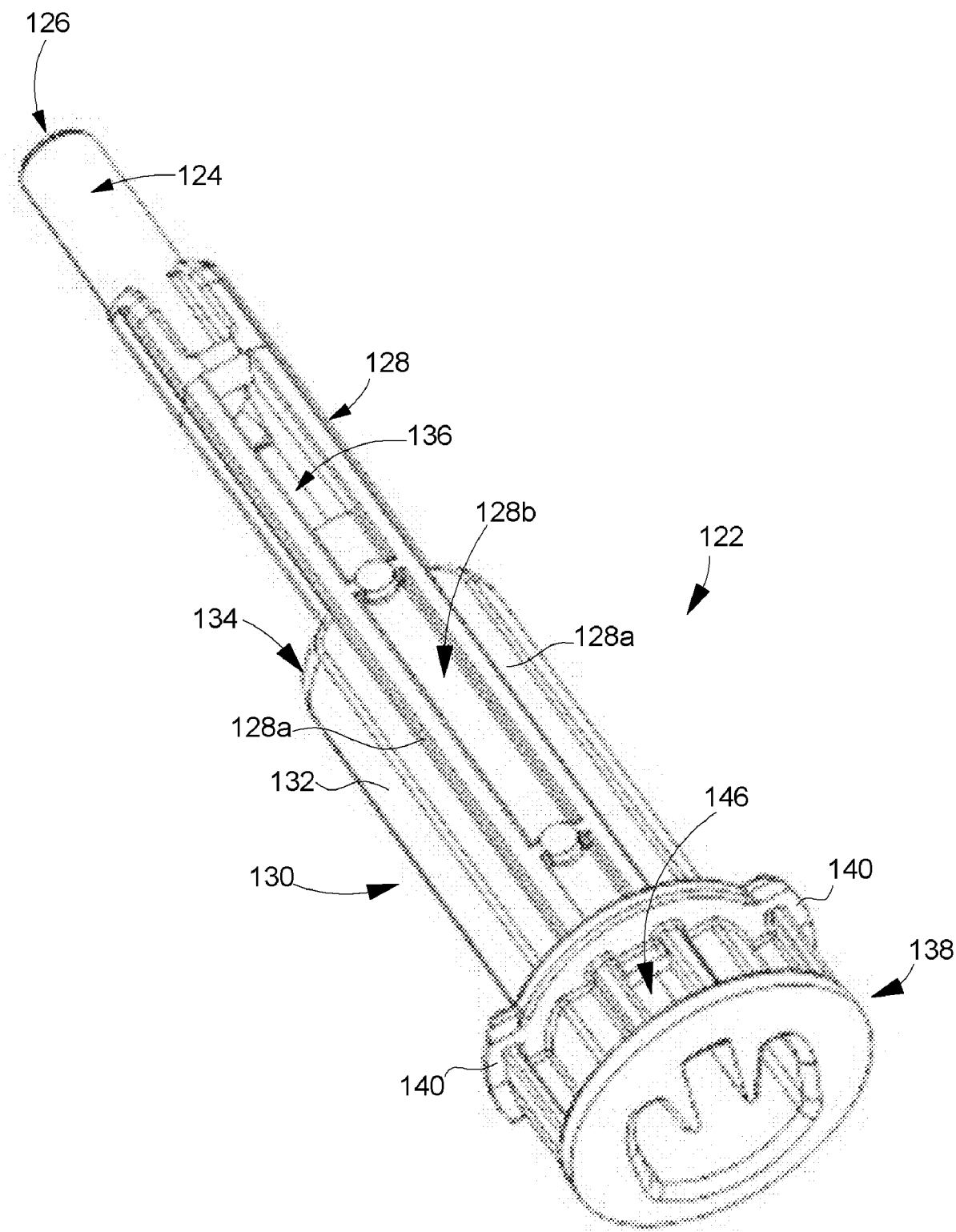
FIGS. 25A and 25B are perspective views along two different angles of the base of the needle according to a second embodiment.
Figure 25B:
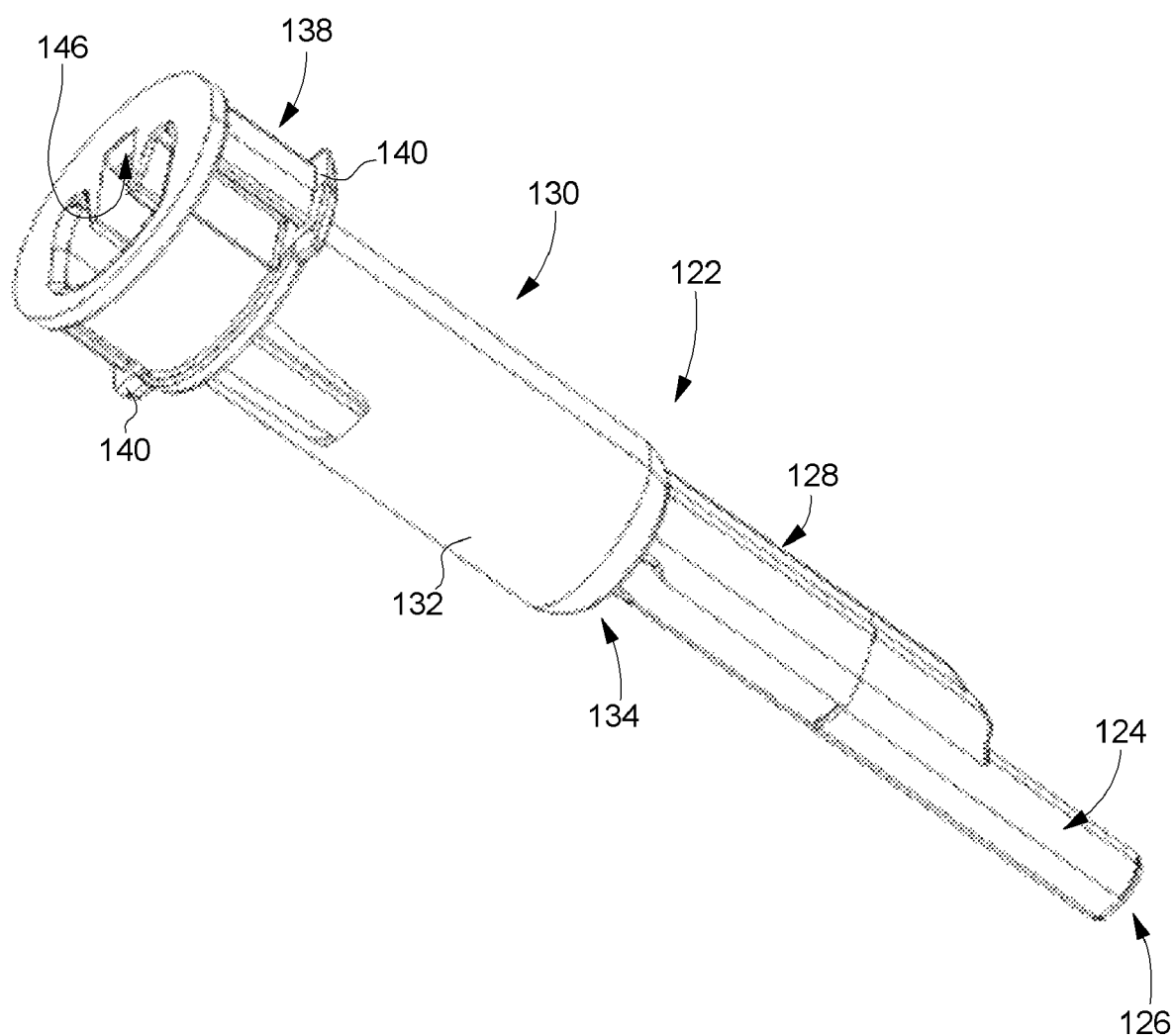
Figure 32:
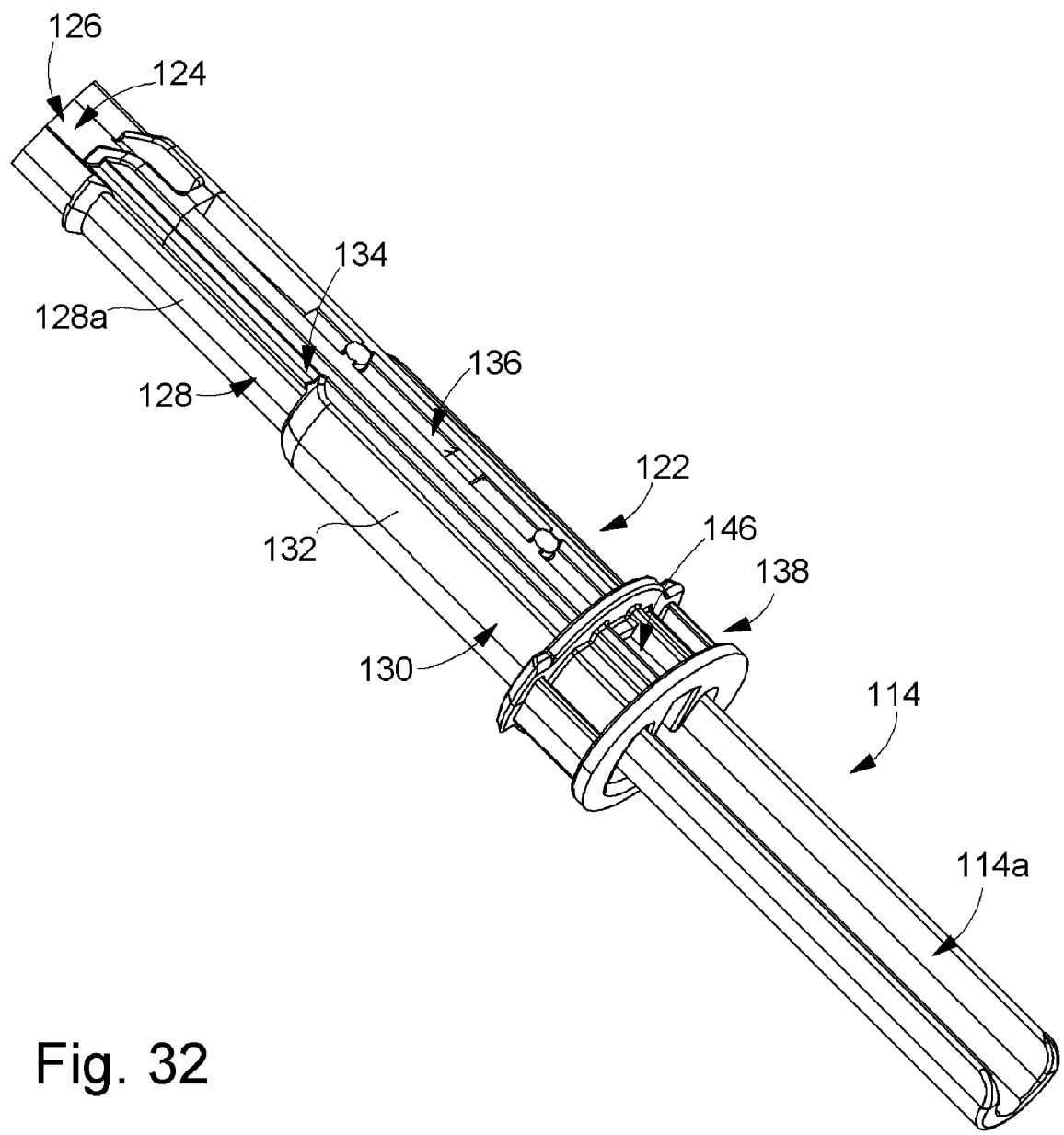
FIG. 32 is a perspective view showing the cooperation between the secondary body and the base according to the second embodiment.

A preferred variant of back-injection device 1 according to the invention will now be examined. Elements that are identical to those described in conjunction with the preceding embodiment are designated by the same reference numeral sand will not be described further here. According to this preferred embodiment of the invention, the secondary body, designated here by the reference numeral 114, comprises only a single tube portion 114a, which substantially corresponds to half of the cylindrical envelope in which said secondary body 114 is inscribed (see FIGS. 24A and 24B). This tube portion 114a thus delimits an aperture 116 into which a longitudinal elastic arms 118 extends, ending at the free end thereof in a raised portion 129 oriented on the inner side of said tube 114a. The base of hollow needle 28 (see FIGS. 25A and 25B), designated here by the reference 122, essentially comprises one tube portion 124, which defines a through aperture 126 for friction holding and/or bonding said needle 28 and which is extended by a rectilinear groove 128, which has a straight U-shaped cross-section for cooperating with the shape of secondary body 114. The body 130 of base 122 is formed by a cylinder portion 132, which is attached to the opposite vertical flanks 128a of groove 128 so as to delimit an annular passage 134 in which tube portion 114a of secondary body 114 can slide (see FIG. 32). An aperture 136, whose role will be described below, is also arranged in the bottom 128b of groove 128. Finally, body 130 of base 122 ends in a button 138 comprising two raised portions 140 for projecting into two corresponding apertures 142 arranged at the proximal end of main body 144 for immobilising said base 122 on said main body 144. In this case, end cap 66 provided in the first embodiment, is no longer necessary. A notch 146, in the same plane and in the extension of aperture 136 is also made in button 138.

Figure 26A:
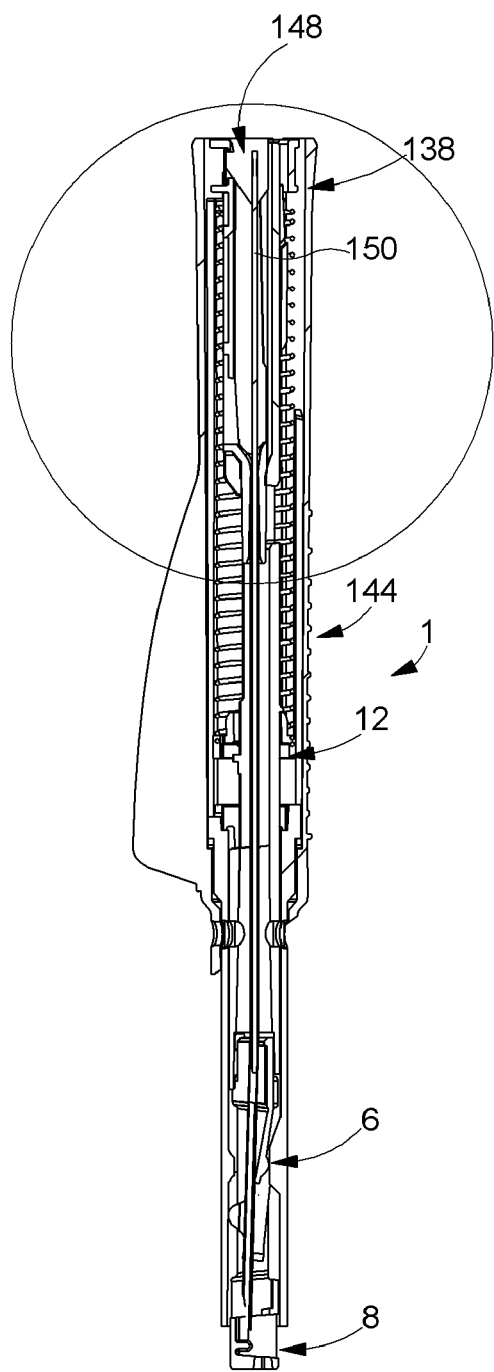
FIG. 26A is a longitudinal cross-section of the back injection device prior to use including a secondary body according to the second embodiment.
Figure 26B:
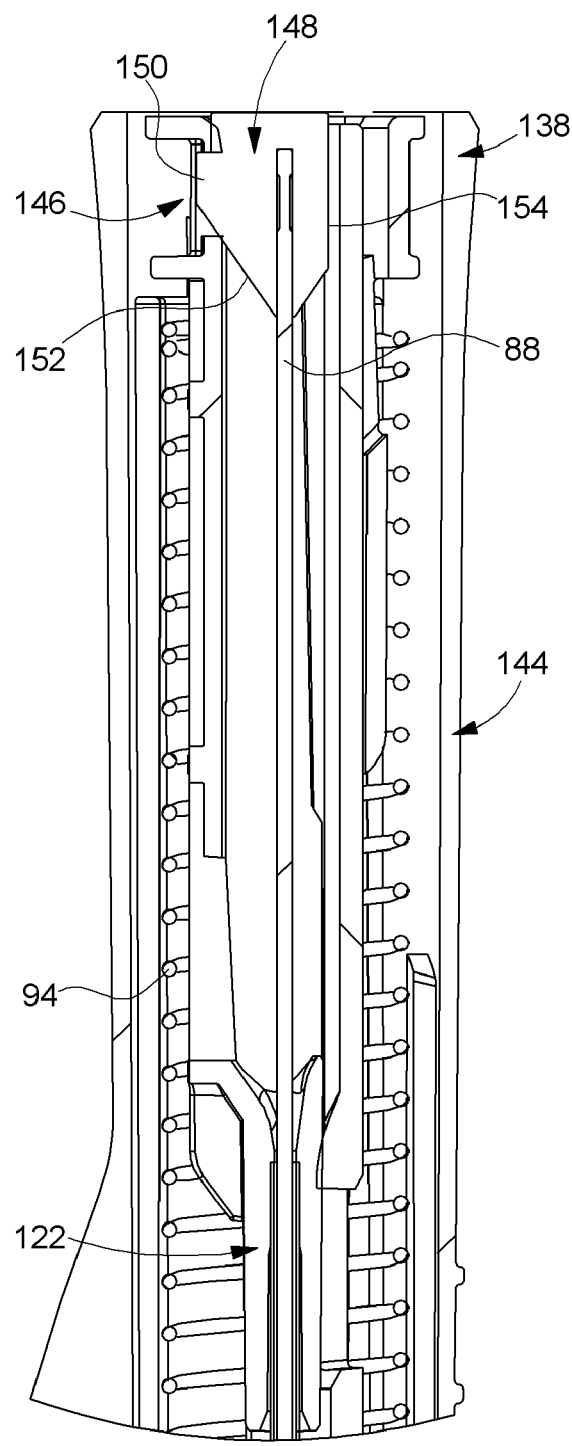
FIG. 26B is a larger scale detail view of the zone surrounded by a circle in FIG. 26A.

The head 148 of piston rod 88 includes a snug 150, which in the storage position of back-injection device 1 according to the invention, projects into notch 146 of button 138, which couples said piston rod 88 to main body 144 via base 122 (see FIG. 26B). Snug 150 of head 148 of piston rod 88 is connected via an inclined plane 152 to a heel 154. Gradually as hollow needle 28 penetrates the subject's skin 22, secondary body 114 moves up inside main body 144 by sliding along base 122 (see FIG. 27B). Shortly before needle 28 is completely pushed in to the subject's skin 22, head 148 of piston rod 88 slides via its heel 154 over the raised portion 120 of elastic arm 118, which moves away from its rest position. Finally, head 148 passes raised portion 120 and its heel 154 falls into aperture 116. At that moment, head 148 of piston rod 88 is coupled on the one hand to main body 144 and on the other to secondary body 114 (see FIG. 27C). Collar 92, changes groove, and spring 94 is compressed to the maximum.

Figure 28A:
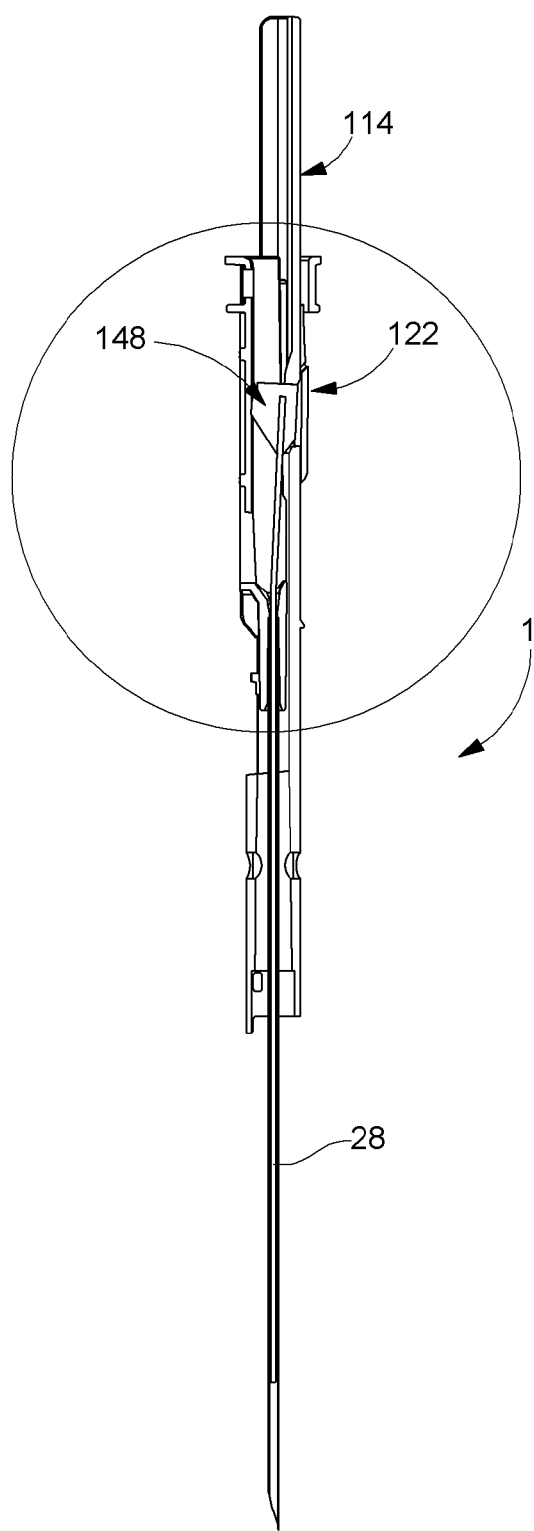
FIG. 28A is a longitudinal cross-section of the back injection device during the phase of withdrawing the needle from the subject's skin.
Figure 28B:
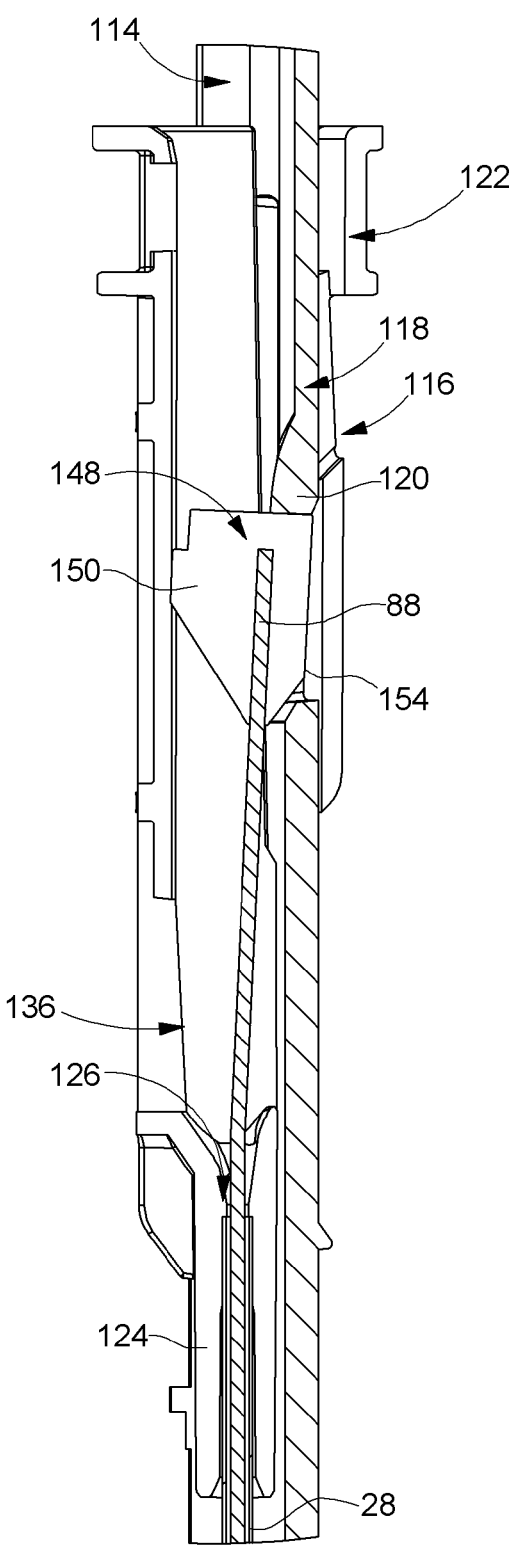
FIG. 28B is a larger scale detail view of the zone surrounded by a circle in FIG. 28A showing the piston rod head secured to the secondary body and sliding via its stud against the inner wall of main body.
Figure 29A:
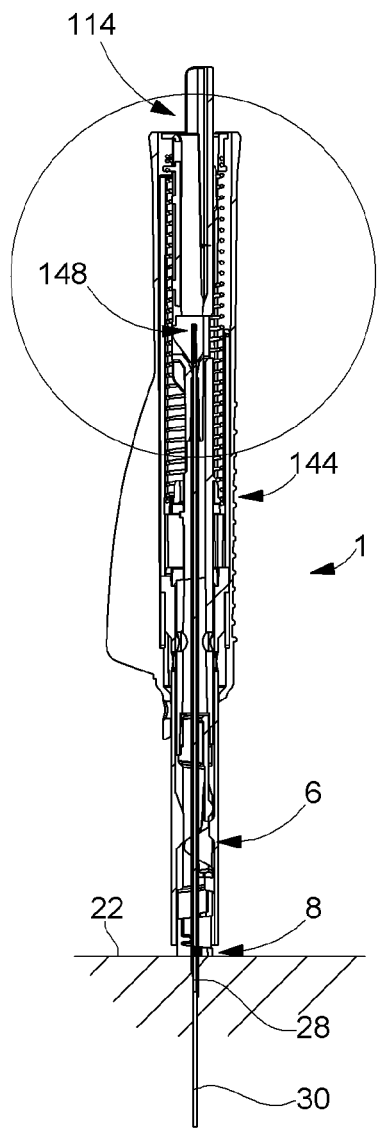
FIG. 29A is a longitudinal cross-section of the back injection device wherein the needle is practically withdrawn from the subject's skin.
Figure 29B:
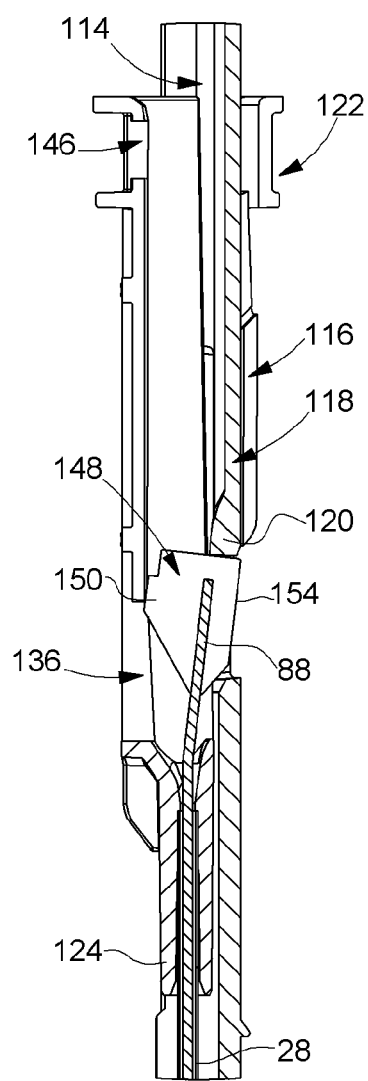
FIGS. 29B and 29C are larger scale views of the zone surrounded by a circle in FIG. 29A, which show how the piston rod head is again coupled to the main body.
Figure 29C:
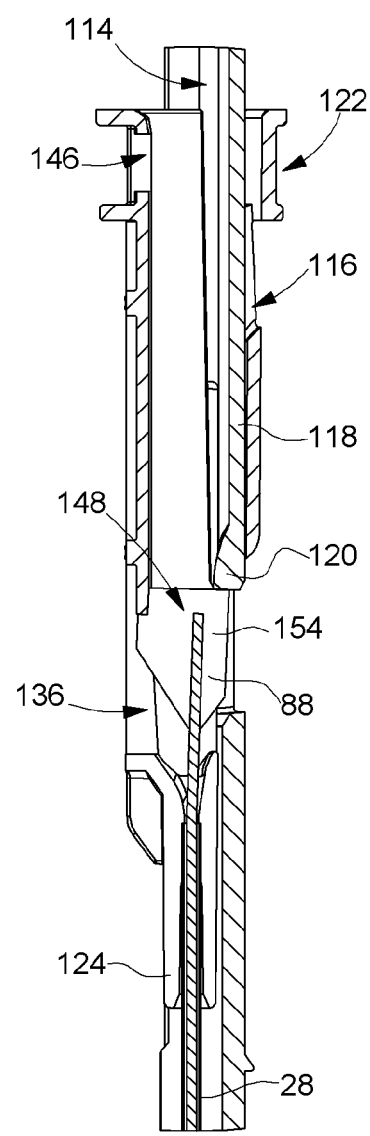
Figure 30:
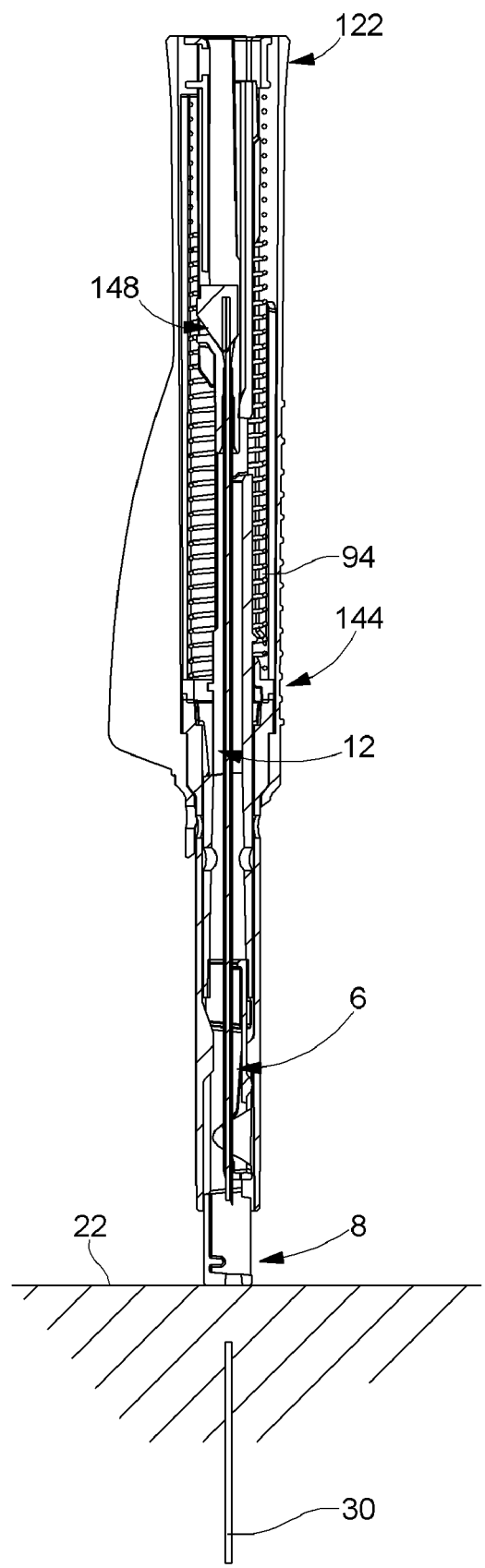
FIG. 30 is longitudinal cross-section of the back injection device in the locked position after injection of the implant, the piston rod head being coupled to the main body.

When the back-injection begins, spring 94 lets down and secondary body 114 again slides along base 122 but in the direction of exit from main body 144 this time. Snug 150 of head 148 of piston rod 88, retained by raised portion 120 (see FIG. 28B), is released from main body 144 and slides along the bottom 128b of groove 128 until the moment that it is facing aperture 136 (see FIGS. 29B and 29C). At this moment, piston rod 88 relaxes and snug 150 penetrates said aperture 136, its heel 154 being released from raised portion 120. Piston rod 88 is thus again coupled to base 122, in other words to main body 144, which allows secondary body 114 to travel the distance necessary for the complete withdrawal of needle 28 from the subject's skin 22 and the protection of the latter inside back-injection device according to the invention (see FIG. 30). In this position, implant 30 has been maintained at the correct depth in the subject's skin 22, all that remains is to finish removing needle 28 and piston rod 88 from skin 22. In order to do this, piston rod 88, again secured to main body 144, is withdrawn concomitantly with needle 28.

Figure 31:
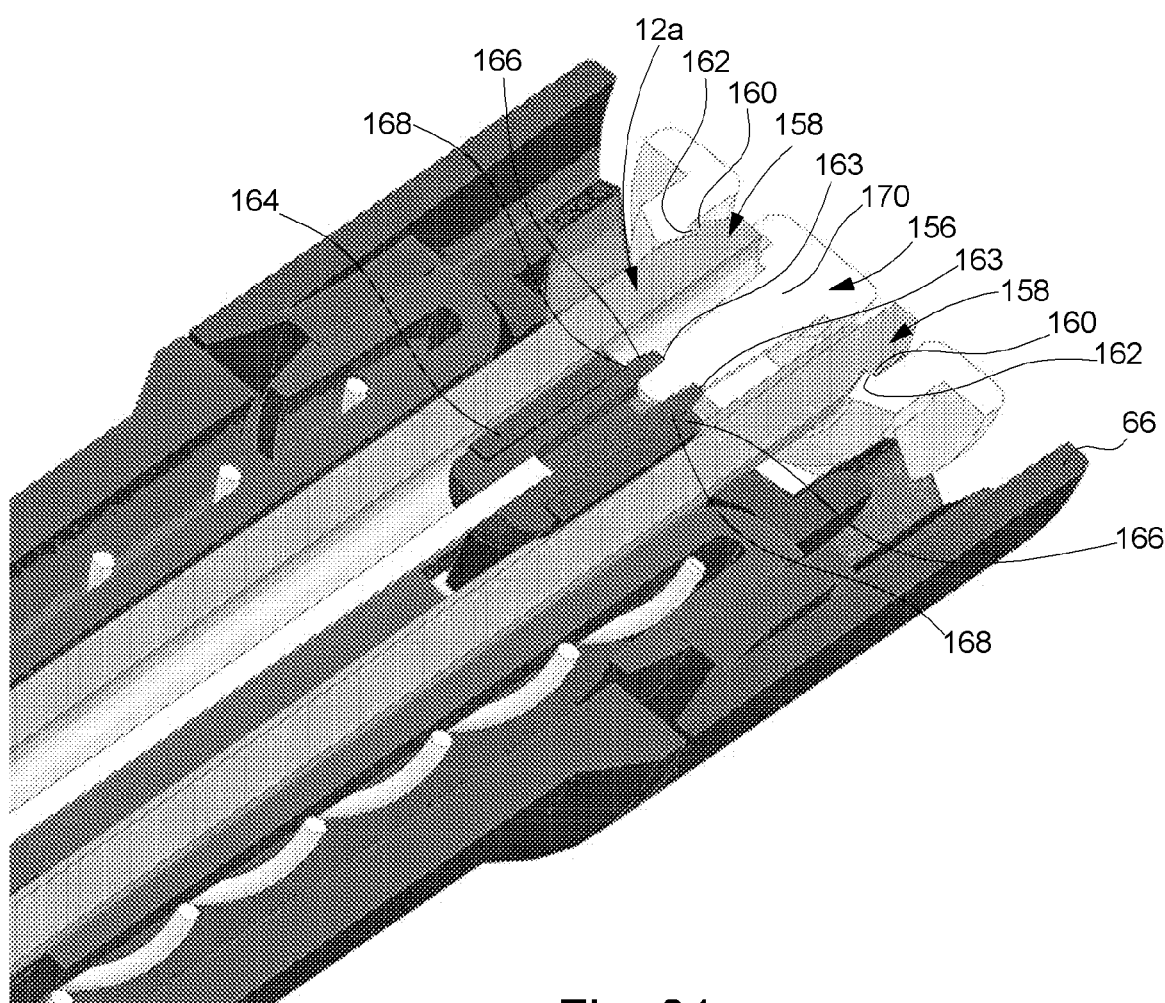
FIG. 31 is a partial perspective view and cross-section of the back end of the back injection device showing another method of coupling the piston rod head to the secondary body.

It goes without saying that the present invention is not limited to the embodiments that have just been described and that various simple alterations and variants could be envisaged by those skilled in the art without departing from the scope of the invention as defined by the annexed claims. One could in particular envisage that the spring, instead of being practically let down in the storage position of the back-injection device, is, conversely, compressed and lets down during the return of the secondary body out of the main body. According to a variant shown in FIG. 31, the two tube portions 12a, 12b could be held together by snapping onto a cap 156 during the entire use of back-injection device 1 according to the invention. Thus, the two tube portions 12a, 12b each have a raised portion 158, which defines a catching surface 160 on an inner edge 162 of cap 156. The function of cap 158 is also to temporarily couple head 86 to piston rod 88 and main body 10 in the storage position of back-injection device 1. Thus, head 86 of piston rod 88 takes the form of a pair of clips 163 passed through a central sleeve 164 arranged inside end cap 66 and each having a raised portion 166 defining a catching surface 168 on sleeve 164. In the storage position, clips 163 are held apart from each other by a conical tip 170, which stands on the inner surface of cap 156. When back-injection device 1 is activated, secondary body 12 gradually exits main body 10, such that tip 170 is released from clips 162. The latter are then allowed to move closer to each other and can slide inside sleeve 164, thereby uncoupling head 88 of piston rod 88 from main body 10.

The invention claimed is:

1. A device for back injecting an implant into the skin of a subject, said device including:
   (a) a hollow main body to which a hollow needle is fixed, into which the implant is introduced;
   (b) a secondary body coaxially arranged inside the main body and surrounding the hollow needle, wherein the secondary body is capable of retracting inside the main body;
   (c) a piston rod capable of sliding coaxially inside the hollow needle;
   (d) first means for allowing the piston rod to maintain position unchanged with respect to the hollow needle when the device is pressed against the skin of the subject to allow the hollow needle to penetrate the subject's skin when the secondary body retracts inside the main body, and the first means allows the piston rod to penetrate inside the hollow needle to hold the implant at a required depth in the subject's skin while the hollow needle is withdrawn from the subject's skin during which the secondary body exits the main body; and
   (e) means for elastically returning the secondary body out of the main body, wherein the elastic return means controls exit of the secondary body outside of the main body, wherein the elastic return means automatically releases itself thereby bringing the secondary body to surround again the hollow needle.

2. A device according to claim 1, wherein the elastic return means includes a helical spring.

3. A device according to claim 2, wherein the spring is inserted between the main body and the secondary body.

4. A device according to claim 2, wherein the spring compresses during a phase of retraction of the secondary body inside the main body, then is let down when the hollow needle has reached the maximum depth thereof in the subject's skin, causing automatic return of the secondary body to an exit position thereof out of the main body.

5. A device according to claim 3, wherein the spring compresses during a phase of retraction of the secondary body inside the main body, then is let down when the hollow needle has reached the maximum depth thereof in the subject's skin, causing automatic return of the secondary body to an exit position thereof out of the main body.

6. A device according to claim 4, wherein the spring abuts at one of the ends thereof against a collar that abuts the secondary body and whose other end abuts against a base that carries the hollow needle and that is secured to the main body.

7. A device according to claim 5, wherein the spring abuts at one of the ends thereof against a collar that abuts the secondary body and whose other end abuts against a base that carries the hollow needle and that is secured to the main body.

8. A device according to claim 6, wherein the collar includes at least one snug via which the collar cooperates with at least one first cam path arranged in an inner wall of the main body, and the collar further includes a second cam path via which the collar cooperates with a cam surface arranged on the secondary body.

9. A device according to claim 7, wherein the collar includes at least one snug via which the collar cooperates with at least one first cam path arranged in an inner wall of the main body, and the collar further includes a second cam path via which the collar cooperates with a cam surface arranged on the secondary body.

10. A device according to claim 8, wherein the first cam path includes two longitudinal rectilinear grooves, wherein one groove is shorter than the other groove, and the snug sliding first of all into the shorter groove prior to reaching a point of return where the two grooves communicate with each other and where the collar is no longer guided axially and is forced to pivot via the spring so that the snug penetrates the longer groove of the two grooves.

11. A device according to claim 9, wherein the first cam path includes two longitudinal rectilinear grooves, wherein one groove is shorter than the other groove, and the snug sliding first of all into the shorter groove prior to reaching a point of return where the two grooves communicate with each other and where the collar is no longer guided axially and is forced to pivot via the spring so that the snug penetrates the longer groove of the two grooves.

12. A device according to claim 1, wherein the device includes a retaining element for preventing the implant from falling prior to use of said device.

13. A device according to claim 12, wherein the retaining element includes an elastic tongue, which, in a rest position, blocks a clearance hole for the hollow needle via an end part inclined towards an interior of the volume of the retaining element, and which, when the back injecting device is pressed against the subject's skin, moves away to free a passage for said hollow needle.

14. A device according to claim 12, wherein the retaining element includes an elastic tongue above which the hollow needle passes and which, in a storage position of the device, is bent towards an interior of the volume of the retaining element so that the hollow needle is moved away from a general direction of forward movement thereof, and the elastic tongue returns to a rest position in which the elastic tongue allows the hollow needle to be realigned and to move forward when the device is pressed against the subject's skin.

15. A device according to claim 1, wherein the device further includes a sheath that cooperates with the secondary body for irreversibly locking the device after use.

16. A device according to claim 15, wherein the secondary body locks onto the sheath that locks onto the main body.

17. A device according to claim 16, wherein the sheath includes at least one elastic arm, which, after the device has been used, is moved away from a rest position thereof by the secondary body and is housed via a free end thereof in a slot provided on the secondary body, wherein the elastic arm further includes at a free end thereof a snug that projects into a housing arranged at a distal end of the main body.

18. A device according to claim 17, wherein the sheath also temporarily locks the device prior to use.

19. A device according to claim 18, wherein the secondary body has on a periphery thereof an inclined plane via which said secondary body holds the elastic arm in the housing in a storage position of the device.

20. A device according to claim 13, further comprising a sheath that cooperates with the secondary body for irreversibly locking the device after use, wherein the sheath cooperates with the retaining element to free the passage for the hollow needle.

21. A device according to claim 20, wherein the sheath has, on an inner periphery of a distal end thereof at least one inclined plane that abuts on the elastic tongue when the device is pressed against the subject's skin so that said tongue moves away from the rest position thereof and frees the passage for the needle, or a snug, which, in the storage position of the device, bends the elastic tongue towards an inside of the volume of the retaining element, wherein said snug moves away from said elastic tongue that returns to the rest position thereof and allows the hollow needle to align with a general axis of forward movement thereof when said device is pressed against the subject's skin.

22. A device according to claim 21, wherein the sheath includes two inclined planes between which a rib slides, provided on the retaining element for indexing position of the retaining element inside the sheath.

23. A device according to claim 21, wherein the retaining element includes a groove into which the snug slides for indexing position of the retaining element relative to the sheath.

24. A device according to claim 10, further comprising a sheath that cooperates with the secondary body for irreversibly locking the device after use, wherein position of the sheath relative to the main body is indexed by at least one snug that is engaged in the longest groove of the first cam path.

25. A device according to claim 6, wherein the base includes a first tube portion that defines a through aperture for holding the hollow needle and that is connected to a hollow cylindrical body of the base by at least one rib.

26. A device according to claim 25, wherein the base is capped by a cap inside which there extends a sleeve, and a bar extending diametrically inside said sleeve.

27. A device according to claim 26, wherein the secondary body is a hollow body of substantially cylindrical shape provided with two diametrically opposite rectilinear slots that extend from a proximal end of the secondary body to a height above a distal end of the device, wherein said slots embody two second tube portions that pass right through the first tube portion and an interior of the hollow cylindrical body of the base, and then pass right through a bar prior to penetrating an interior of the sleeve.

28. A device according to claim 27, wherein the two second tube portions include locking means.

29. A device according to claim 28, wherein the piston rod includes a head via which the piston rod is coupled to the bar to be driven by the main body when the hollow needle penetrates the subject's skin, and via which the piston rod cooperates with the locking means in order to be uncoupled from the main body and coupled to the secondary body when the hollow needle is withdrawn from the subject's skin.

30. A device according to claim 6, wherein the base includes a first tube portion that defines a through hole for holding the hollow needle and that is extended by a rectilinear groove on opposite flanks to which a cylinder portion is attached so as to delimit an annular passage, and an aperture is arranged in the bottom of the rectilinear groove, and the base further includes at a proximal end thereof a button comprising a notch made therein.

31. A device according to claim 30, wherein secondary body includes a single second tube portion that is capable of sliding into the annular passage, and an elastic arm ending at a free end thereof in a raised portion extending into an aperture arranged in the second tube portion.

32. A device according to claim 31, wherein the piston rod includes a head via which the piston rod is coupled to the button to be driven by the main body when the hollow needle penetrates the subject's skin, and via which the piston rod cooperates with the secondary body to remain immobile when the needle is withdrawn from the subject's skin.

33. A device according to claim 32, wherein the head of the piston rod includes a snug, which, in a storage position of the device, projects into the notch of the button, wherein the snug is connected via an inclined plane to a heel via which the snug slides over the raised portion of the elastic arm and finishes by passing over the raised portion to fall into the aperture, at the moment when the needle is completely pushed into the subject's skin, wherein the snug is subsequently retained by the raised portion that allows the snug to be uncoupled from the main body gradually as the secondary body exits the main body again, until the moment when the snug is facing the aperture and penetrates the aperture, the heel thereof is uncoupled from the raised portion so that the piston rod is again coupled to the main body in order to allow the secondary body to travel a distance necessary for complete withdrawal of the hollow needle from the subject's skin.

* * * * *